(12) United States Patent
Akuzawa et al.

(10) Patent No.: US 10,627,360 B2
(45) Date of Patent: Apr. 21, 2020

(54) AIR PHYSICAL QUANTITY SENSOR

(71) Applicant: DENSO CORPORATION, Kariya, Aichi-pref. (JP)

(72) Inventors: Hiroyuki Akuzawa, Kariya (JP); Takashi Enomoto, Kariya (JP); Junzo Yamaguchi, Kariya (JP); Takuma Tsuchiya, Kariya (JP)

(73) Assignee: DENSO CORPORATION, Kariya (JP)

( * ) Notice: Subject to any disclaimer, the term of this patent is extended or adjusted under 35 U.S.C. 154(b) by 218 days.

(21) Appl. No.: 15/715,566

(22) Filed: Sep. 26, 2017

(65) Prior Publication Data

US 2018/0120248 A1 May 3, 2018

(30) Foreign Application Priority Data

Oct. 28, 2016 (JP) .................. 2016-212115

(51) Int. Cl.
*G01N 27/22* (2006.01)
*G01N 33/00* (2006.01)
*G01N 27/12* (2006.01)
*A61B 5/145* (2006.01)

(52) U.S. Cl.
CPC ....... *G01N 27/223* (2013.01); *A61B 5/14546* (2013.01); *G01N 27/121* (2013.01); *G01N 27/22* (2013.01); *G01N 27/225* (2013.01); *G01N 33/0011* (2013.01); *G01N 33/0036* (2013.01)

(58) Field of Classification Search
CPC .. G01N 27/223; G01N 27/225; G01N 27/121; G01N 27/22; A61B 5/14546
USPC ..................................... 73/335.04
See application file for complete search history.

(56) References Cited

U.S. PATENT DOCUMENTS

| | | | | |
|---|---|---|---|---|
| 2002/0040598 A1* | 4/2002 | Sugaya | ............... | G01N 27/121 73/335.02 |
| 2002/0190840 A1* | 12/2002 | Fujita | .................. | G01N 27/121 338/35 |
| 2004/0237646 A1* | 12/2004 | Fujita | .................. | G01N 27/121 73/335.05 |

(Continued)

FOREIGN PATENT DOCUMENTS

| | | |
|---|---|---|
| JP | 2016-109625 | 6/2016 |
| WO | 2018/079035 | 5/2018 |

OTHER PUBLICATIONS

International Search Report PCT/JP2017/030232, International Searching Authority, dated Nov. 14, 2017, 2 pgs (Year: 2017).*

(Continued)

*Primary Examiner* — Clayton E. LaBalle
*Assistant Examiner* — Kevin C Butler
(74) *Attorney, Agent, or Firm* — Nixon & Vanderhye PC

(57) ABSTRACT

A sensor body has a body recess portion, in which a sensor element is housed and the body recess portion opens at a body opening portion. A sensor cover has a cover window which communicates between the intake passage and the body opening portion, and the sensor cover covers the sensor body. A sensor filter is provided with a sensor peripheral portion which extends along a virtual surface. In a projection view with respect to the virtual plane the body opening portion and the cover window are positioned within a filtering area which is defined as an inner side of a contour of the filter peripheral portion, such that the filter peripheral portion contacts the sensor body and the sensor cover.

10 Claims, 31 Drawing Sheets

(56) References Cited

U.S. PATENT DOCUMENTS

| | | | | |
|---|---|---|---|---|
| 2011/0072894 A1* | 3/2011 | Saito | ............... | F02D 41/187 73/114.34 |
| 2012/0198925 A1* | 8/2012 | Saito | ............... | F02D 41/187 73/114.33 |
| 2013/0269419 A1* | 10/2013 | Etherington | ............ | G01F 1/692 73/37 |
| 2014/0283596 A1* | 9/2014 | Hosokawa | ............ | G01N 27/121 73/335.02 |
| 2015/0177037 A1* | 6/2015 | Wagner | ............ | G01N 27/048 73/204.22 |
| 2015/0260672 A1* | 9/2015 | Kaufmann | ............ | F02D 41/18 73/29.05 |
| 2015/0260673 A1* | 9/2015 | Seto | ............ | G01N 33/0059 73/335.03 |
| 2015/0377671 A1* | 12/2015 | Ooga | ............ | G01F 1/6842 73/114.32 |
| 2016/0097661 A1* | 4/2016 | Hidaka | ............ | G01F 1/34 73/114.33 |
| 2016/0139071 A1* | 5/2016 | Nakano | ............ | F02M 35/10386 73/23.31 |
| 2016/0290893 A1* | 10/2016 | Itakura | ............ | G01N 27/121 |
| 2017/0016415 A1* | 1/2017 | Hoshika | ............ | G01N 27/223 |
| 2017/0082051 A1* | 3/2017 | Hoshika | ............ | F02D 41/18 |
| 2017/0315104 A1* | 11/2017 | Kono | ............ | G01N 33/0006 |
| 2018/0120248 A1* | 5/2018 | Akuzawa | ............ | G01N 27/223 |
| 2018/0274964 A1* | 9/2018 | Yamaguchi | ............ | G01F 15/14 |
| 2019/0170551 A1* | 6/2019 | Tsuchiya | ............ | G01F 1/684 |

OTHER PUBLICATIONS

Written Opinion of the International Search Authority PCT/JP2017/030232, International Searching Authority, dated Nov. 14, 2017, 4 pgs (Year: 2017).*

U.S. Appl. No. 16/267,421 of Tsuchiya et al., filed Feb. 5, 2019 (61 pages).

* cited by examiner

AIR PHYSICAL QUANTITY SENSOR

CROSS REFERENCE TO RELATED APPLICATION

This application is based on Japanese Patent Application No. 2016-212115 filed on Oct. 28, 2016, the disclosure of which is incorporated herein by reference.

FIELD

The present disclosure relates to an air physical quantity sensor that detects a specified quantity of an air flowing in a fluid passage.

BACKGROUND

Conventionally, an air physical quantity sensor has a sensor element for outputting the detected signal in accordance with a specified quantity, the sensor element housed in a recess portion of a sensor body, which opens at an opening portion.

In the sensor as an air physical quantity sensor as shown in Japanese Patent application No. 2015-187603 (referred to as patent document 1, hereinafter), the atmosphere sensor has a sensor filter in a sensor case. The moisture permeable film is bonded to the case by a welding method.

The moisture permeable film having the shape of a circle or an oval and the welded part having the shape of a ring make bonded strength between the welded part and the bottom surface of the sensor case uniform. Since a restoring force continually acts to the welded part and the welded part is easily removed, the moisture permeable film is separated from the case. The moisture permeable film having extensibility make the mesh enlarge, and the filter performance is reduced.

The present disclosure is made in view of the above matters, and it is an object of the present disclosure to provide an air physical quantity sensor, a sensor filter of which is prevented to remove and to deform.

SUMMARY

A sensor body has a body recess portion, in which a sensor element is housed and the body recess portion opens at a body opening portion. A sensor cover has a cover window which communicates between the intake passage and the body opening portion, and the sensor cover covers the sensor body. A sensor filter is provided with a sensor peripheral portion which extends along a virtual surface. In a projection view with respect to the virtual plane the body opening portion and the cover window are positioned within a filtering area R which is defined as an inner side of a contour of the filter peripheral portion, such that the filter peripheral portion contacts one of the sensor body and the sensor cover.

The filter peripheral portion positions between the sensor body and the sensor cover and contacts one of the sensor body and the sensor cover, such that a shape of the sensor filter extending along the virtual plane can be maintained and the sensor filter is prevented to remove from between the sensor body and the sensor cover.

The body opening portion is positioned in the cover window in the projection view.

In the projection view with respect to the virtual plane, the body opening portion is positioned in the cover window within the filtering area. The air flowing through the cover window and the sensor filter from the intake passage entries into the body recess from the body opening portion without being blocked by the sensor body around the body opening portion. The air from the intake passage easily reaches to the sensor element in the body recess. Since the sensor filter extending along the virtual plane is interposed between the sensor body and the sensor cover, the sensor filter is positioned near to the sensor element in the body recess. As a result, since an inner volume of the body recess is small, a time of the air flowing from the intake passage to the sensor element can be shortened. Accordingly, since the air easily reaches to the sensor element and the air reaching time to the sensor element is also minimized, the detection response of the sensor element can be enhanced.

DETAILED DESCRIPTION

Figure 1:
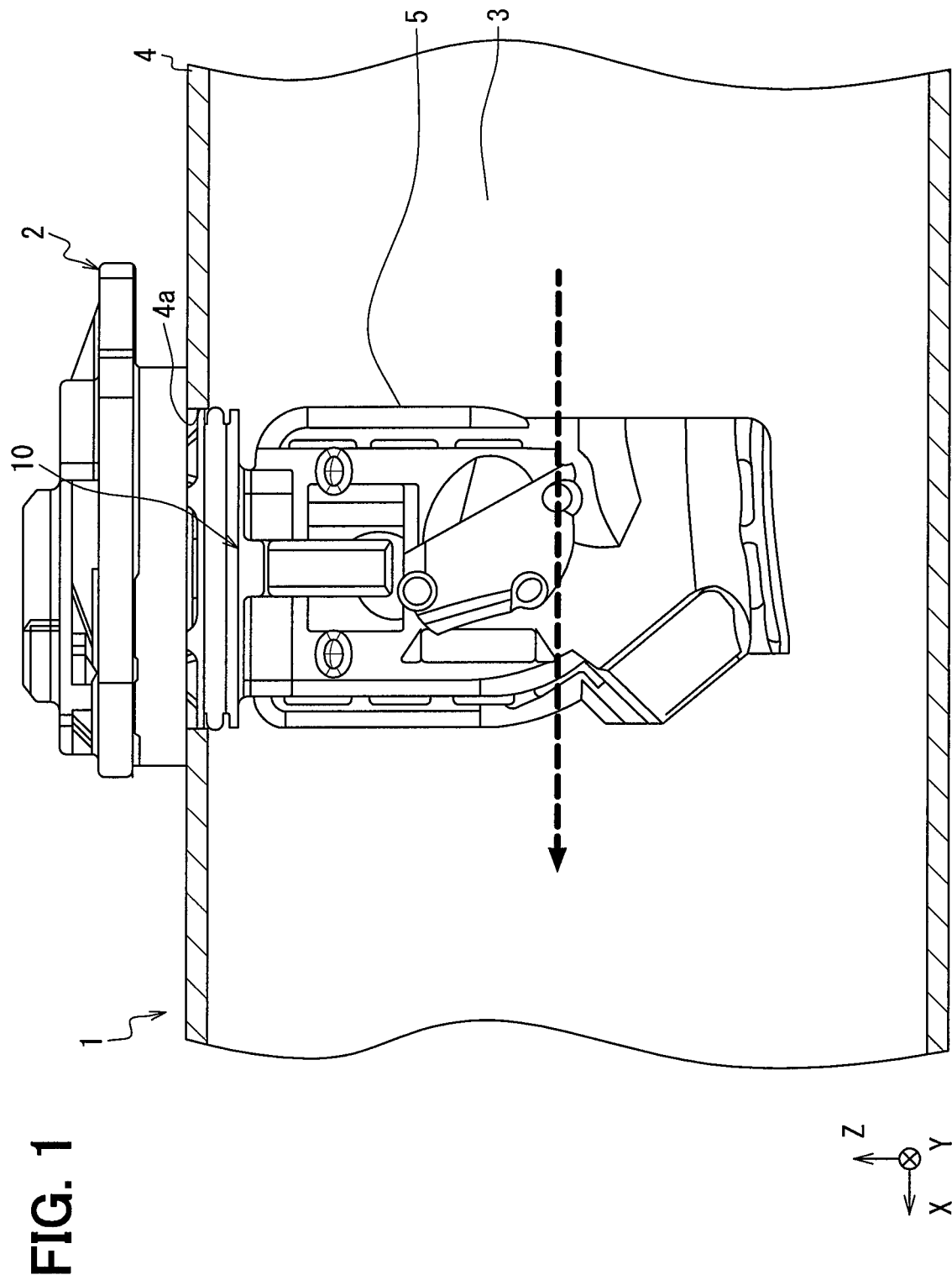
FIG. 1 is a diagram illustrating a partial cross-sectional view, showing an air physical quantity sensor attached to an air flow detection unit in an internal combustion engine.

In the following, embodiments of the present disclosure are described with reference to the accompanying drawings. In the description and in the drawings, identical or similar components bear the same reference numerals or characters. If a part of the features in each embodiment is explained, the remaining part of the features may apply to the remaining part of the features in other embodiments. In each embodiment, a combination of the features is disclosed in the specification, and in addition to the combination, the features in the embodiments may be combined, even if such combinations are not apparently disclosed in the specification.

First Embodiment

As shown in FIG. 1, an air physical quantity sensor 10 is applied to an air flow detection unit 2 in an internal combustion engine.

Figure 2:
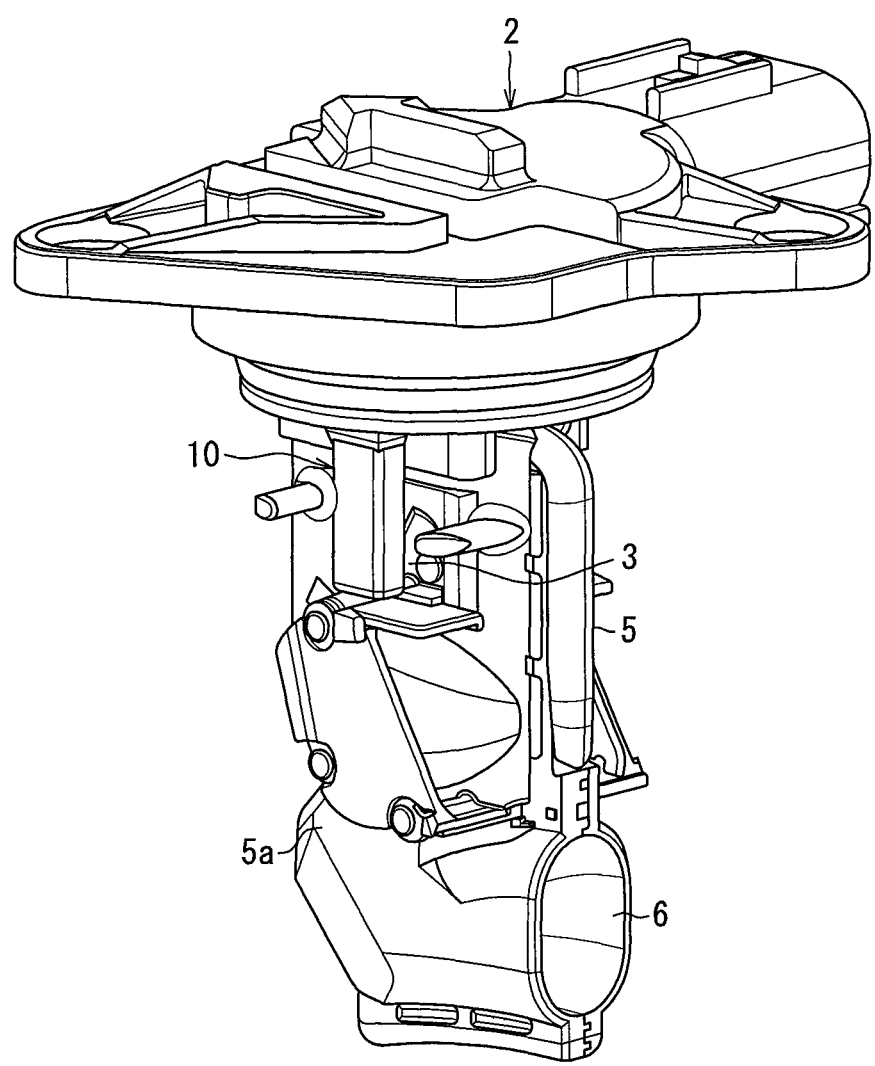
FIG. 2 is a diagram illustrating a perspective view, showing the air flow detection unit provided with the air physical quantity sensor in a first embodiment.
Figure 3:
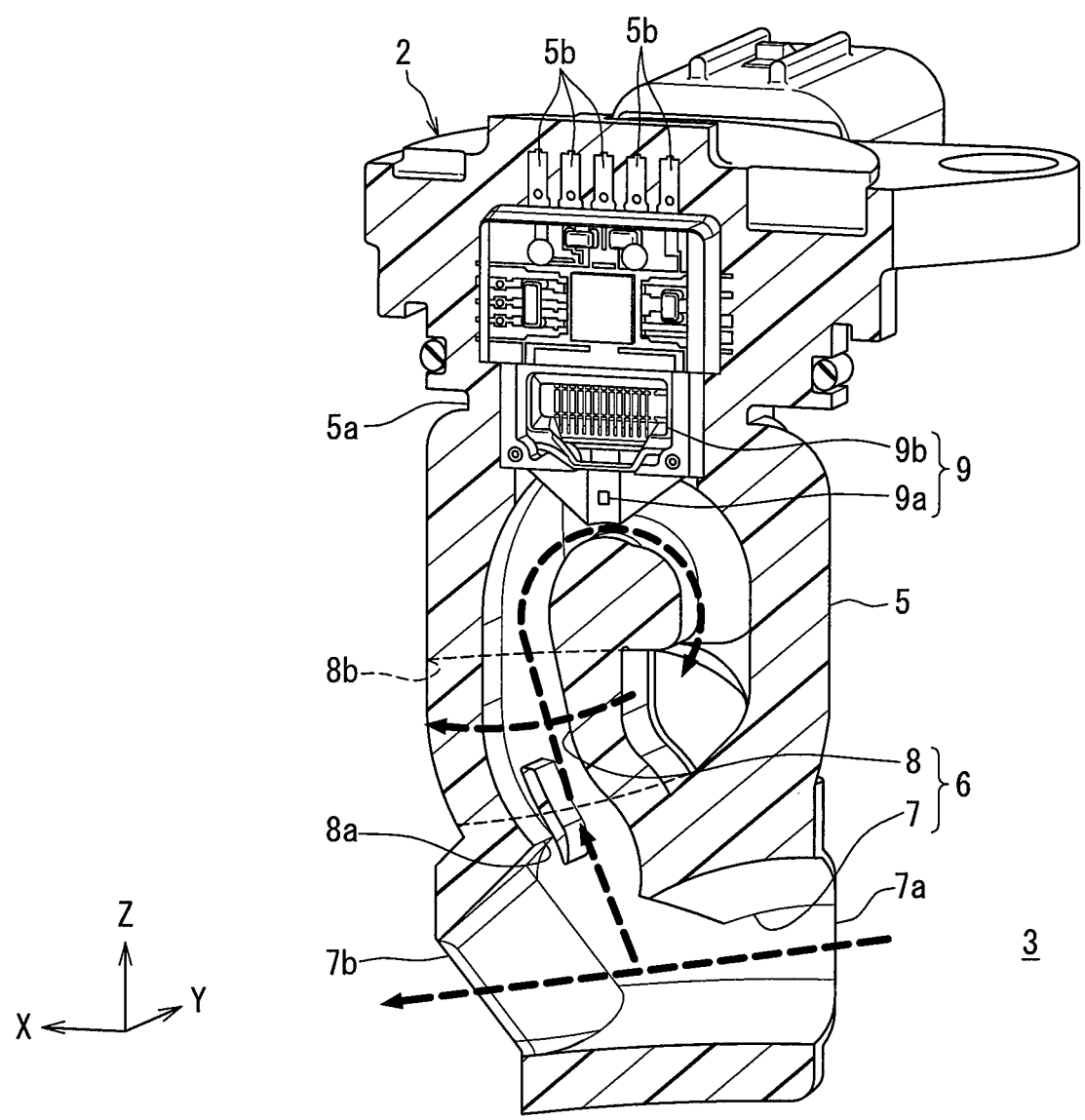
FIG. 3 is a diagram illustrating a perspective and partial cross-sectional view showing the air flow detection unit in the first embodiment.

The air flow detection unit 2 is attached to an attachment opening 4a of an intake air duct 4 formed as an intake passage 3 in the internal combustion engine. The air flow detection unit 2 is provided with a flow detection body 5 located in the intake passage 3. As shown in FIGS. 2 and 3, the flow detection body 5 has a bypass passage 6 in a detection portion 5a. Along an arrow of the broken line shown in FIGS. 1 and 3, a part of the intake air flowing into a cylinder of the internal combustion engine through the intake passage 3 is distributed in the bypass passage 6 from the intake passage 3.

As shown in FIG. 3, the bypass passage 6 comprises a first passage portion 7 and a second passage portion 8. The straight first passage portion 7 includes an inlet 7a and an outlet 7b, both of which open the intake passage 3. In a direction of an arrow of the dashed line shown in FIG. 3, the first passage portion 7 introduces the intake air in a substantially same direction along the intake passage 3 from the inlet 7a to the outlet 7b. The curved second passage portion 8 comprises an inlet 8a facing a middle part of the first passage portion 7, and an outlet 8b facing the intake passage 3, such that the second passage portion 8 is branched from the first passage portion 7. In the direction of the arrow of the dashed line shown in FIG. 3, the second passage portion 8 whirls the intake air in an opposite direction with respect to the intake passage 3 and then flows the intake air in a same direction along the intake passage 3 between the inlet 8a and the outlet 8b.

The flow detection body 5 further includes a flow sensor 9 and the above mentioned bypass passage 6. A sensor element 9a of the flow sensor 9 is exposed to the second passage portion 8. The sensor element 9a outputs a flow signal depending on an amount of intake air flowing in the second passage portion 8. The flow sensor 9 includes a circuit module 9b, which calculates the amount of the intake air in the intake passage 3 based on the flow signal outputted from the sensor element 9a. The amount of intake air calculated by the circuit module 9b is transmitted to an engine control unit provided outside of the intake passage 3 via a signal transmission through a plurality of terminals 5b in the flow detection body 5. The flow detection body 5 detects the amount of the intake air flowing in the intake passage 3 by means of the sensor element 9a.

As shown in FIGS. 1 and 2, the air physical quantity sensor 10 is integrally provided with the air flow detection unit 2. The air physical quantity sensor 10 is arranged outside of the bypass passage 6 such that the sensor 10 is exposed to the intake passage 3 referred to as flow passage. The air physical quantity sensor 10 is configured to have a predetermined width extending in the intake air flow direction in the intake passage 3 in the direction of the arrow of the dashed line shown in FIG. 3, and the air physical quantity sensor 10 is configured to be formed as thick belt shape extending in a vertical direction with respect to the intake air flow direction as a whole. X direction is defined as the intake air flow direction in the intake passage 3. Z direction is defined as a longitudinal direction in which the air physical quantity sensor 10 extends in the vertical direction with respect to the flow direction. Y direction is defined as a vertical direction with respect to both X direction and Z direction.

Figure 4:
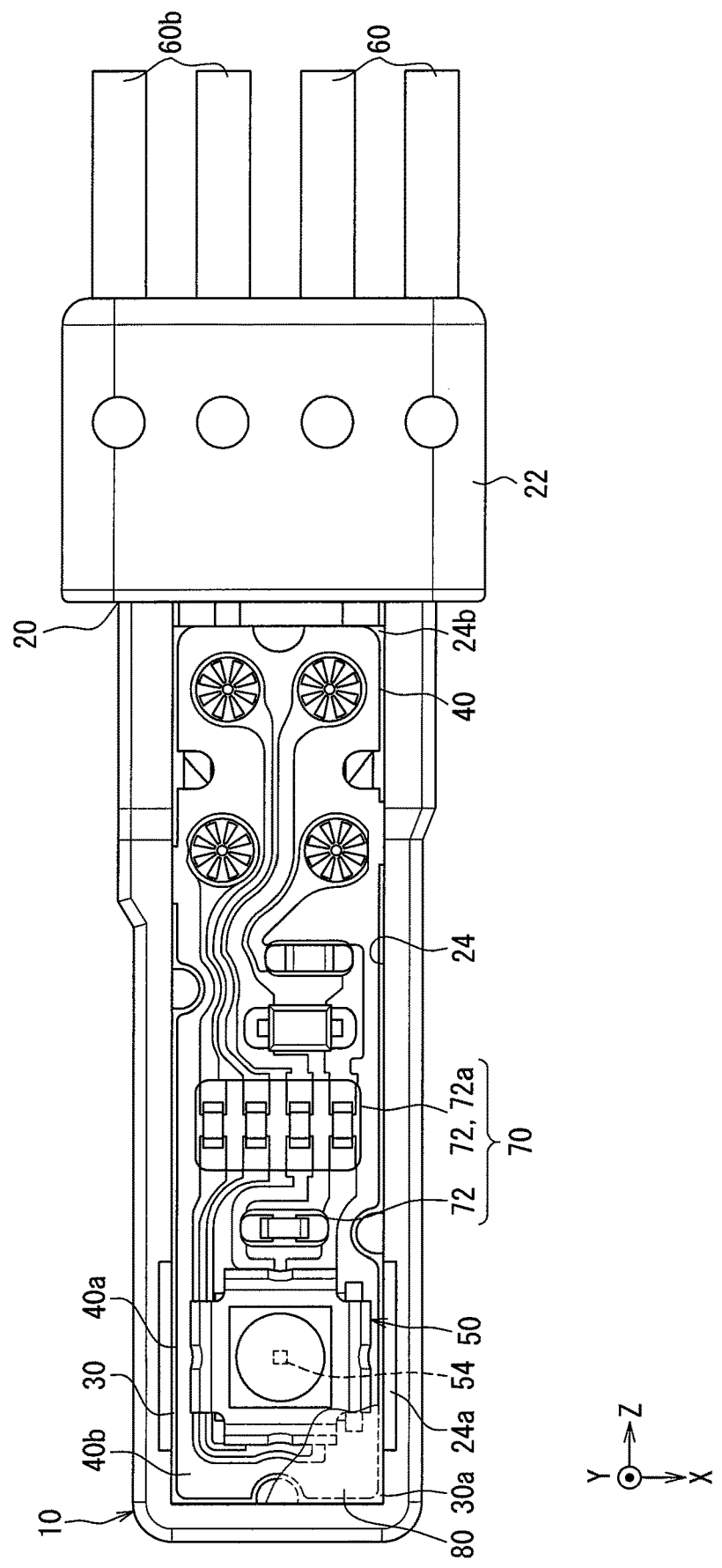
FIG. 4 is a diagram illustrating a plan view showing the air physical quantity sensor in the first embodiment.
Figure 5:
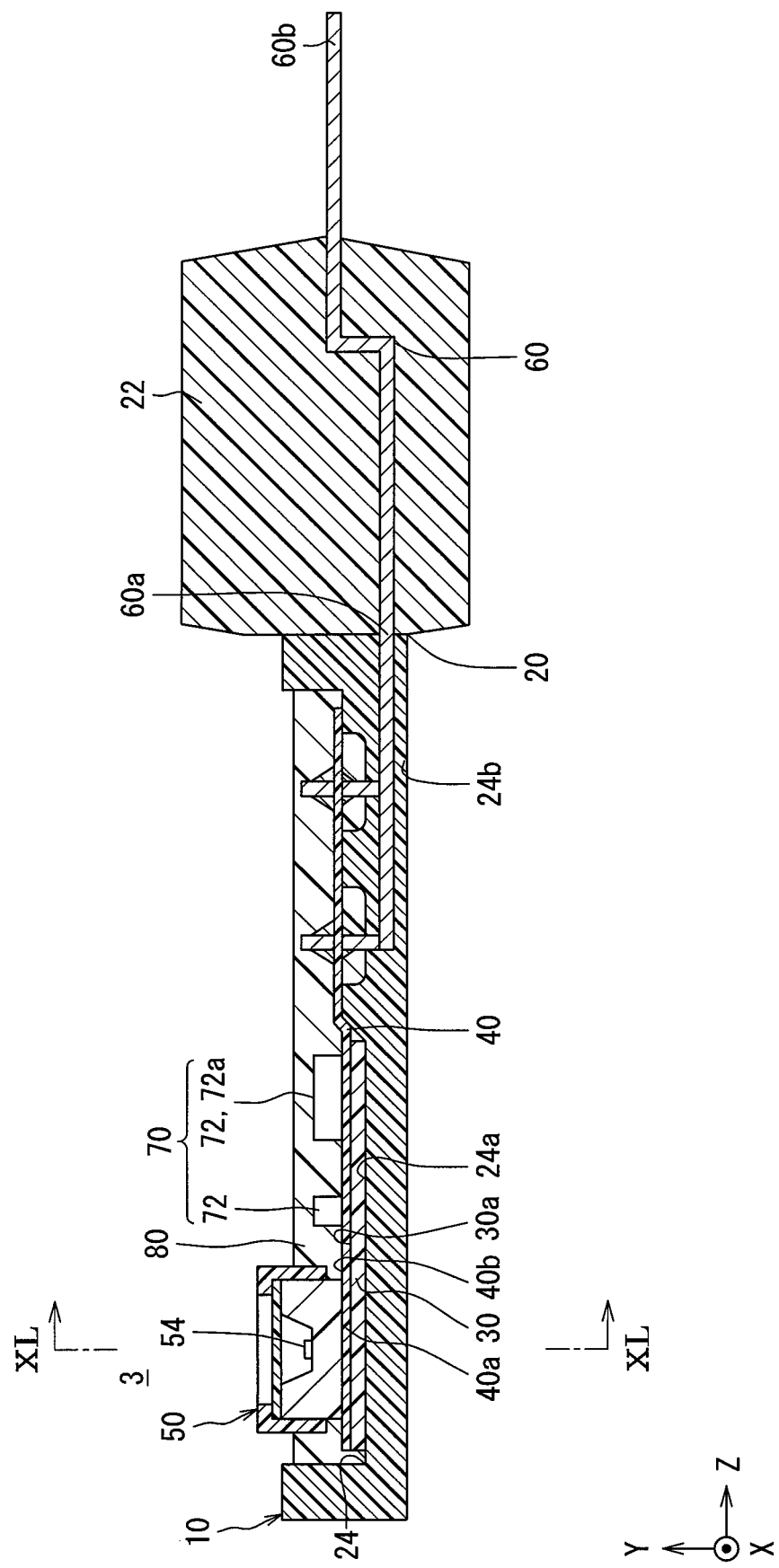
FIG. 5 is a diagram illustrating a cross-sectional view showing the air physical quantity sensor in the first embodiment.

As shown in FIGS. 4 and 5, the air physical quantity sensor 10 includes a sensor case 20, a reinforced plate 30, a sensor substrate 40, a sensor unit 50, a terminal 60, a circuit module 70, and a potting resin portion 80. For better understanding, a part of the potting resin portion 80 is shown in FIG. 4.

The sensor case 20 is made of a hard resin, such as polyphenylene sulfide (PPS). The sensor case 20 is formed as thick belt shape, corresponding to a whole contour of the air physical quantity sensor 10. The sensor case 20 has a connector portion 22 and a recess portion 24. The connector portion 22 is provided at one end in Z direction as the longitudinal direction of the sensor case 20. The recess portion 24 faces in Y direction toward the flow detection body 5, and The recess portion 24 has a bottomed rectangular shape in planar view in Y direction. After other components 30, 40, 50 and 60 are housed in the recess portion 24, the potting resin 80 is filled into the recess portion 24.

The reinforced plate 30 is made of a metal, such as stainless steel. The reinforced plate 30 is formed as a narrow-width and short thin belt shape in comparison with the sensor case 20. The reinforced plate 30 is positioned and fixed on a bottom surface 24a of the recess portion 24 in a surface contact state. The reinforced plate 30 is embedded by the potting resin 80 in the recess portion 24.

The sensor substrate 40 is made of a soft resin, such as polyimide, and is called as flexible printed board. The sensor substrate 40 is formed as a narrow-width and short shape in comparison with the sensor case 20, and the sensor substrate 40 is formed as a narrow-width and long thin belt shape in comparison with the reinforced plate 30. The sensor substrate 40 is positioned and fixed on a reinforced surface 30a of the reinforced plate 30 on the opposite side of the bottom surface 24a of the recess portion 24 in a surface contact state. The sensor substrate 40 is embedded by the potting resin 80 in the recess portion 24, and a part 40a of the sensor substrate 40 in Z direction as a longitudinal direction is reinforced by the reinforced plate 30. The sensor substrate 40 is provided with a mounting surface 40b in a reinforced part 40a, which is formed as a planar surface positioned on the opposite side of the reinforced plate 30.

The sensor unit 50 has a sensor element 54 which detects humidity representing a ratio of water vapor in the intake air. Humidity is referred to as specified physical quantity relating to the intake air flowing in the intake passage 3. The sensor element 54 of the sensor unit 50 outputs a humidity signal, referred to as a detection signal in accordance with the humidity of the intake air as a detecting target. The sensor unit 50 is formed as a rectangular shape as a whole. The sensor unit 50 is mounted on the mounting surface 40b in the reinforced part 40a on the sensor substrate 40. A part of the sensor unit 50 in Y direction is embedded by the potting resin 80 in the recess portion 24, and a remaining part of the sensor unit 50 in Y direction is exposed to the intake passage 3 positioned outside of the sensor case 20.

A plurality of terminals 60 are provided. Each of the terminals 60 is made of a metal, such as phosphor bronze. Each of the terminals 60 is formed as a narrow-width and short thin belt shape in comparison with the sensor case 20. Each of the terminals 60 is disposed substantially in parallel in X direction each other. A part 60a of each of the terminals 60 in Z direction is embedded in the sensor case 20 toward the connector portion 22 from the bottom wall 24b formed as the bottom surface 24a of the recess portion 24. Other part 60b of each of the terminals 60 in Z direction is protruded toward outside of the sensor case 20 from the connector portion 22. The other part 60b of each of the terminals 60 is electrically connected to the engine control unit via any one of the terminals in the air flow detection unit 22. It is preferable that each of the terminals 60 is formed as thin having a thickness of 0.2 mm (for example), and is functioned as a low thermal conductivity. So, a heat insulating function is obtained between an outside including the engine control unit, and the circuit module 70 and the sensor element 54 such that a detection error due to increasing of a temperature of the sensor element 54 can be suppressed.

The circuit module 70 is electrically connected to the sensor element 5 and each of the terminals 60 through a metal conductor provided on the sensor substrate 40. The circuit module 70 includes a plurality of circuit elements 72 for processing a humidity signal outputted from the sensor element 54. Each of the circuit elements 72 is mounted on the mounting surface 40b in the reinforced part 40a on the sensor substrate 40. A control circuit 72a in the circuit elements 72 calculates the humidity of the intake air in the intake passage 3 based on the humidity signal. The humidity calculated by the control circuit 70 is sent to the engine control unit by means of the signal through each of the terminals 60.

The potting resin 80 is made of a hard thermoset resin, such as an epoxy resin or a polyurethane, etc. The potting resin 80 covers almost of the recess portion 24. So, the potting resin 80 covers the mounting surface 40b such that all circuit elements 72 on the mounting surface 40b are sealed. An electrical short between the circuit elements 72 and a damage of the circuit elements 72 are suppressed because the circuit elements 72 are sealed.

(Sensor Unit)

The sensor unit 50 is explained in detail below.

Figure 6:
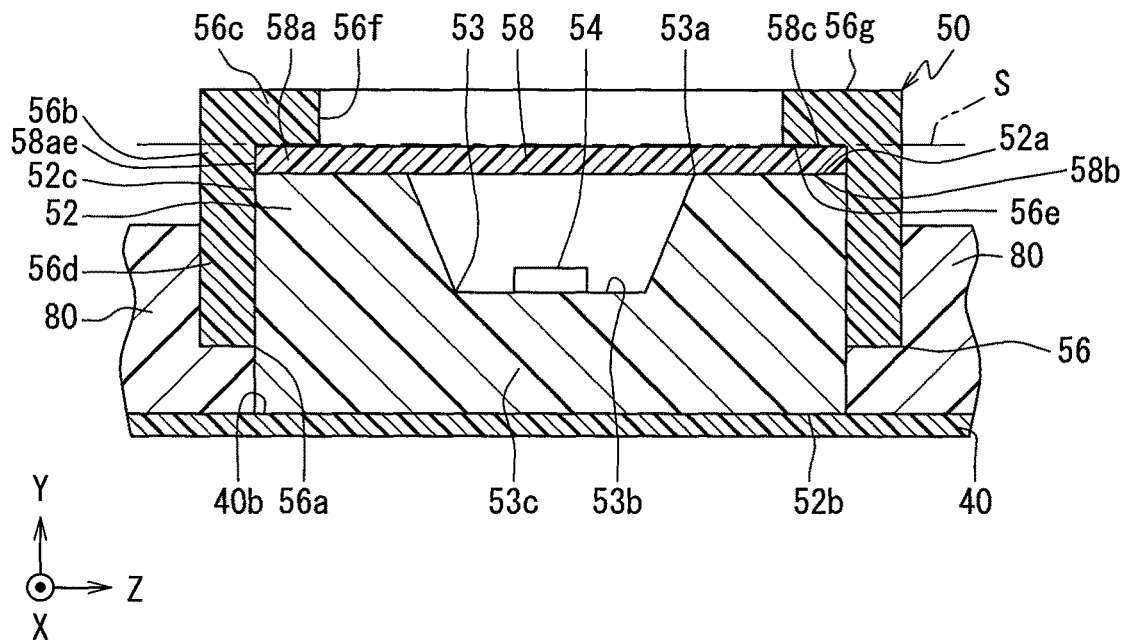
FIG. 6 is a diagram illustrating a cross-sectional view showing the sensor unit in the first embodiment.
Figure 7:
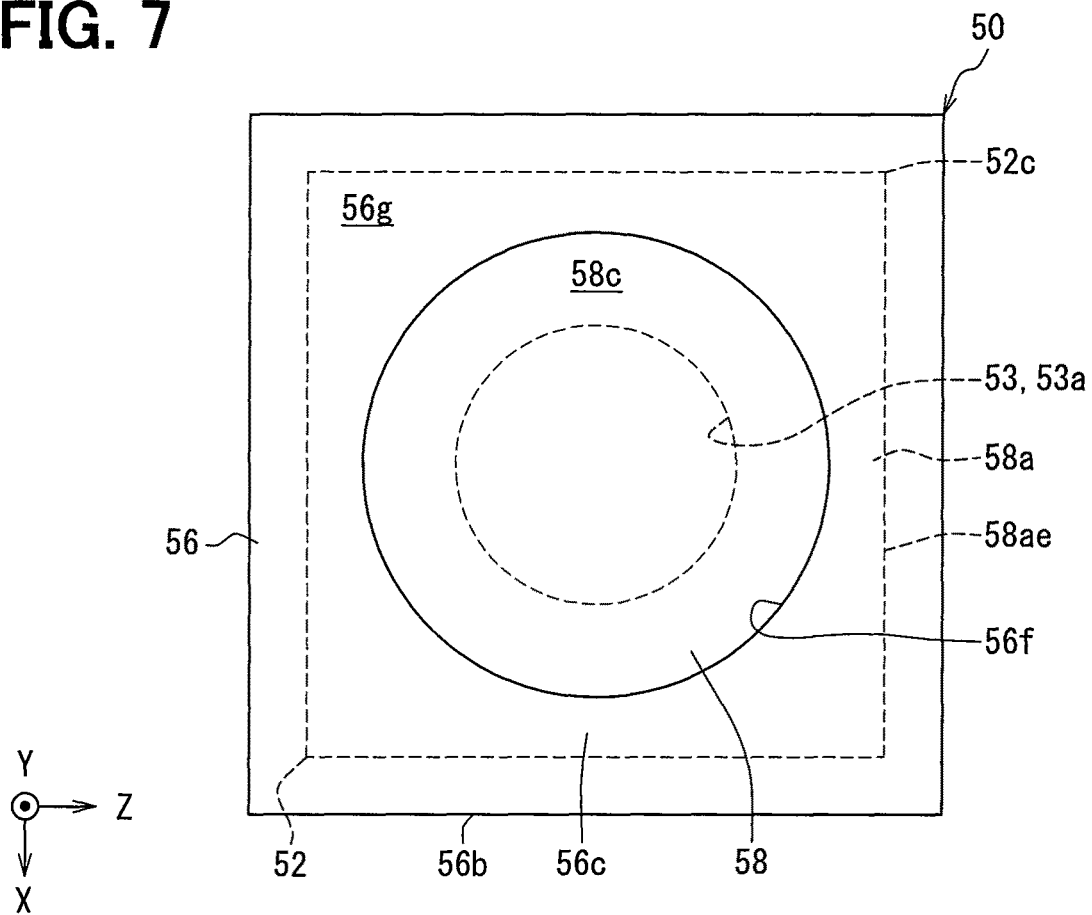
FIG. 7 is a diagram illustrating a plan view showing the sensor unit in the first embodiment.

As shown in FIGS. 6 and 7, the sensor unit 50 has a sensor body 52, a sensor element 54, a sensor cover 56, and a sensor filter 58.

The sensor body 52 according to FIG. 6 is formed of a thermoset resin, such as an epoxy resin, etc. The sensor body 52 is formed as a rectangular shape having 6 (six) surfaces along each direction of X, Y and Z directions. One surface 52b of the sensor body 52 is positioned and fixed on the mounting surface 40b of the sensor substrate 40 in a surface contact state such that the sensor body 52 is held on the mounting surface 40b.

The sensor body 52 has a body recess 53. As shown in FIGS. 6 and 7, the body recess 53 is provided at a central portion in X and Z directions. The body recess 53 opens in the opposite side of the sensor substrate 40 in Y direction, and is formed as a circle bottomed hole in planar view in Y direction. The body recess 53 is formed in the opposite surface 52a of the sensor body 52 with respect to the mounting surface 40b, and opens at an body opening portion 53a. The body recess 53 according to the first embodiment is formed as a truncated cone hole shape such that a diameter becomes gradually larger toward the body opening portion 53a from a bottom surface 53b.

As shown in FIG. 6, the sensor element 54 senses the humidity of the intake air based on a change of a dielectric constant in a polymer film due to a predetermined correlation with respect to the humidity change of the intake air flowing in the intake passage 3. The sensor element 54 is positioned and fixed on the bottom surface 53b separated from the body opening portion 53a, and the sensor element 54 is housed in the body recess 53. The sensor element 54 is electrically connected to a metal conductor on the sensor substrate 40 through a metal conductor (not shown) which is embedded on a bottom wall 53c forming as the bottom surface 53b of the body recess 53 in the sensor body 52. So, the sensor element 54 is configured to output a humidity signal, which varies electrically based on the sensed humidity to the circuit module 70 according to FIGS. 4 and 5.

As shown in FIG. 6, the sensor cover 56 is made of a hard resin, such as PPS or polybutylene terephthalate (PBT), in order to minimize a difference in thermal expansion coefficients with respect to at least the sensor case 20 and the potting resin 80. As shown in FIGS. 6 and 7, the sensor cover 56 opens in a side of the sensor substrate 40 in Y direction, and is formed as a bottomed rectangular shape in planar view in Y direction. The sensor cover 56 includes a cover peripheral portion 56b formed as a rectangular tube shape opening at an body opening portion 56a, and a bottom wall portion 56c formed as a rectangular plate shape closing the cover peripheral portion 56b in an opposite side of the body opening portion 56a in Y direction. The cover peripheral portion 56b and the bottom wall portion 56c are integrally formed.

An inner surface of the cover peripheral portion 56b is fitted to the sensor body 52 along Y direction. The cover peripheral portion 56b surrounds total outer surface of the sensor body 52. As shown in FIG. 6, the cover peripheral portion 56b has the body opening portion 56a in an opposite side of the bottom wall portion 56c in Y direction. A part 56d of the cover peripheral portion 56b extending from the body opening portion 56a to the bottom wall portion 56c is positioned and fixed in the potting resin 80. The cover peripheral portion 56b is provided with an embedded portion 56d, which is embedded outside of the sensor body 52 from the body opening portion 56a by the potting resin 80.

Figure 8:
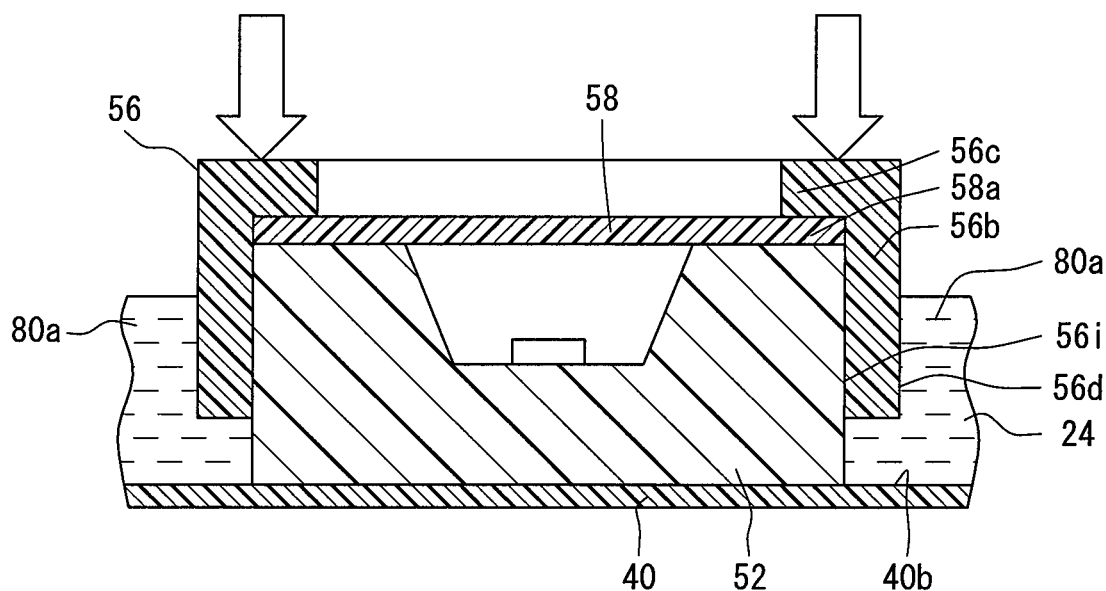
FIG. 8 is a diagram illustrating a schematic diagram showing a method for manufacturing the sensor unit in the first embodiment.

In order to manufacture the sensor unit 50, when the sensor cover 56 is embedded and fixed in the potting resin 80, a thermosetting resin 80a as a forming material of the potting resin 80 fills into the recess portion 24 in a melting state and is cooled thereafter. Since a load toward the bottom surface 24a of the recess portion 24 and in the arrow direction in FIG. 8 continues to act on the sensor cover 56, a floating of the sensor cover 56 due to an inner pressure of the thermosetting resin 80a is prevented, and all area of the embedded portion 56d is embedded continuously. The thermosetting resin 80a is cured on the mounting surface 40b of the sensor substrate 40, and the embedded portion 56d of the cover peripheral portion 56b is embedded and fixed in the potting resin 80.

Since the thermosetting resin 80a heat-shrinks by cooling and curing, a fixing strength of the cover peripheral portion 56b by the potting resin 80 can be enhanced. Since the thermosetting resin 80a is entered into a gap between the sensor body 52 and the cover peripheral portion 56b from the body opening portion 56a, and is cooled and cued thereafter, the fixing strength of the cover peripheral portion 56b by the potting resin 80 can be further enhanced. The embedded portion 56d is embedded and fixed in the potting resin 80 by cooling and curing of the thermosetting resin 80a, and a peripheral portion 58a of the sensor filter 58 (later explained) is held between the sensor body 52 and the bottom wall portion 56c.

As shown in FIGS. 6 and 7, the bottom wall portion 56c is continuously formed substantially vertical to the cover peripheral portion 56b at an opposite side of the body opening portion 56a in Y direction. The peripheral portion 56a fits outside of the sensor body 52, and the peripheral portion 56a is embedded in the potting resin 80. The bottom wall portion 56c covers the sensor body 52 from the opposite side of the sensor substrate 40 in Y direction. A part of the intake passage 3 is formed between an outer surface 56g in the opposite side of the bottom wall portion 56c with respect to the sensor body 52 and the detection portion 5a of the flow detection body 5 according to FIG. 2. As shown in FIG. 6, the outer surface 56g of the bottom wall portion 56c exposes the intake passage 3. An inner surface 56e of the bottom wall portion 56c in the opposite side of the outer surface 56g is separated in Y direction from an opposite surface 52a opposite to the mounting surface 40b with respect to the sensor body 52.

As shown in FIGS. 6 and 7, a cover window 56f is formed as penetrating the bottom wall portion 56c at a central portion in X and Z directions. The cover window 56f faces the intake passage 3 and is separated from the body opening portion 53a. The cover window 56f is provided between the intake passage 3 and the body opening portion 53a, and penetrates the bottom wall portion 56c in Y direction. The cover window 56f is formed as a circle penetrating hole shape (cylindrical hole shape) in planar view in Y direction.

As shown in FIG. 6, the sensor filter 58 is made of a soft resin, such as Polytetrafluoroethylene (PTFE) and is formed as a porous shape. The sensor filter 58 made of PTFE is excellent in a chemical resistance and a heat resistance such that the sensor filter in a hot intake passage 3, in which the intake air including oil flows, hardly deteriorates. Furthermore, a deterioration of a filtering performance is minimized, because a water drop and an oil in the intake air hardly spread in an inside of the sensor filter 58.

As shown in FIGS. 6 and 7, the sensor filter 58 is formed as a flat membrane shape, which is spread along a virtual plane S extending virtually in X and Y directions, and is provided with a filter peripheral part 58a. The filter peripheral part 58a has a rectangular contour 58ae in planar view in Y direction such that the filter peripheral part 58a is surrounded by the cover peripheral portion 56b from outside of the filter peripheral part 58a. In the embodiment according to FIGS. 6 and 7, a size of the contour 58ae of the filter peripheral part 58a is substantially equal to that of an outer contour 52c of the sensor body 52. Within a range satisfied with a formula 1 (later explained), the size of the contour 58ae of the filter peripheral part 58a may be smaller than that of an outer contour 52c of the sensor body 52.

As shown in FIG. 6, one surface 58b of the filter peripheral part 58a in Y direction comes into surface contact to the opposite surface 52a of the sensor body 52 with respect to the mounting surface 40b in a non-joining state. The filter peripheral part 58a comes into surface contact to both the sensor body 52 and the bottom wall portion 56c such that the filter peripheral part 58a is held between the sensor body 52 and the bottom wall portion 56c. In an inner peripheral side positioned inwardly with respect to a holding portion in the sensor filter 58, one surface 58b faces the intake passage 3 through the cover window 56f, and the opposite surface 58c faces the body opening portion 53a in Y direction.

A slight deformation of the sensor filter 58 held between the sensor body 52 and the bottom wall portion 56c may be occurred due to a microscopically roughness of each of the sensor body 52 and the bottom wall portion 56c contacting the filter peripheral part 58a. A specification (for example, dimension and material) for the sensor filter 58, the sensor body 52, and the bottom wall portion 56c, is determined in such a manner that the slight deformation is targeted within a permissible range, not hindering a filtering performance of the sensor filter 58.

Figure 9:
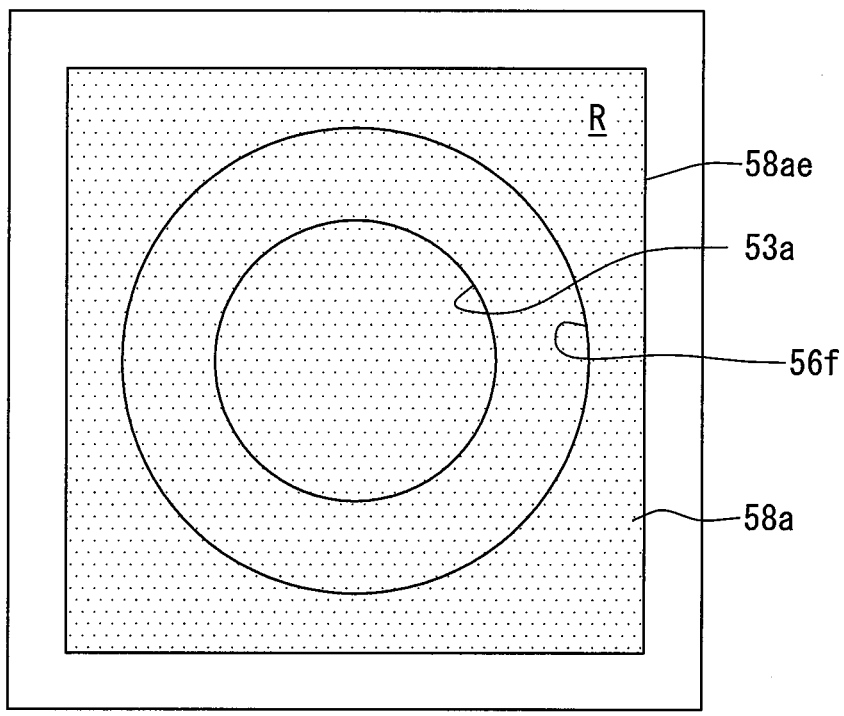
FIG. 9 is a diagram illustrating a schematic diagram showing a detailed configuration of the sensor unit in the first embodiment.

An area in an inner peripheral side positioned inwardly with respect to the contour 58ae of the filter peripheral part 58a in the projection view in Y direction with respect to the virtual plane S is defined as a filtering area R partitioned by dots hatching area in FIG. 9. Under such definition, in the projection view (namely, a projection view in FIG. 9) in Y direction with respect to the virtual plane S, the cover window 56f and the body opening portion 53a are positioned in the filtering area R. In the projection view in Y direction with respect to the virtual plane S, the opening portion body 53a is positioned in the contour of the cover window 56f within the filtering area R.

Figure 10:
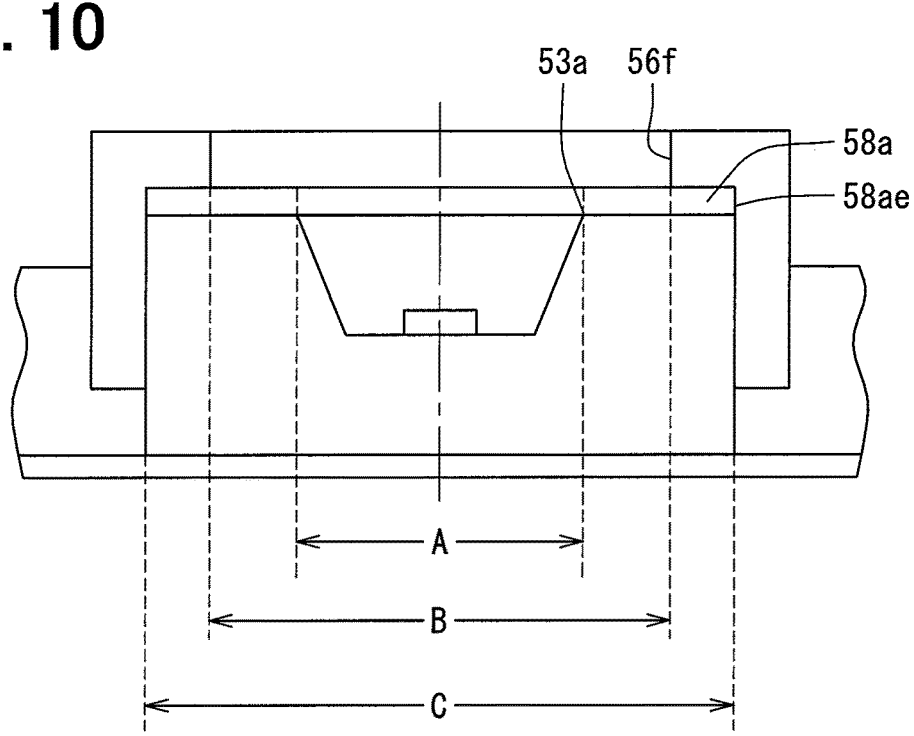
FIG. 10 is a diagram illustrating a schematic diagram showing a detailed configuration of the sensor unit in the first embodiment.
Figure 11:
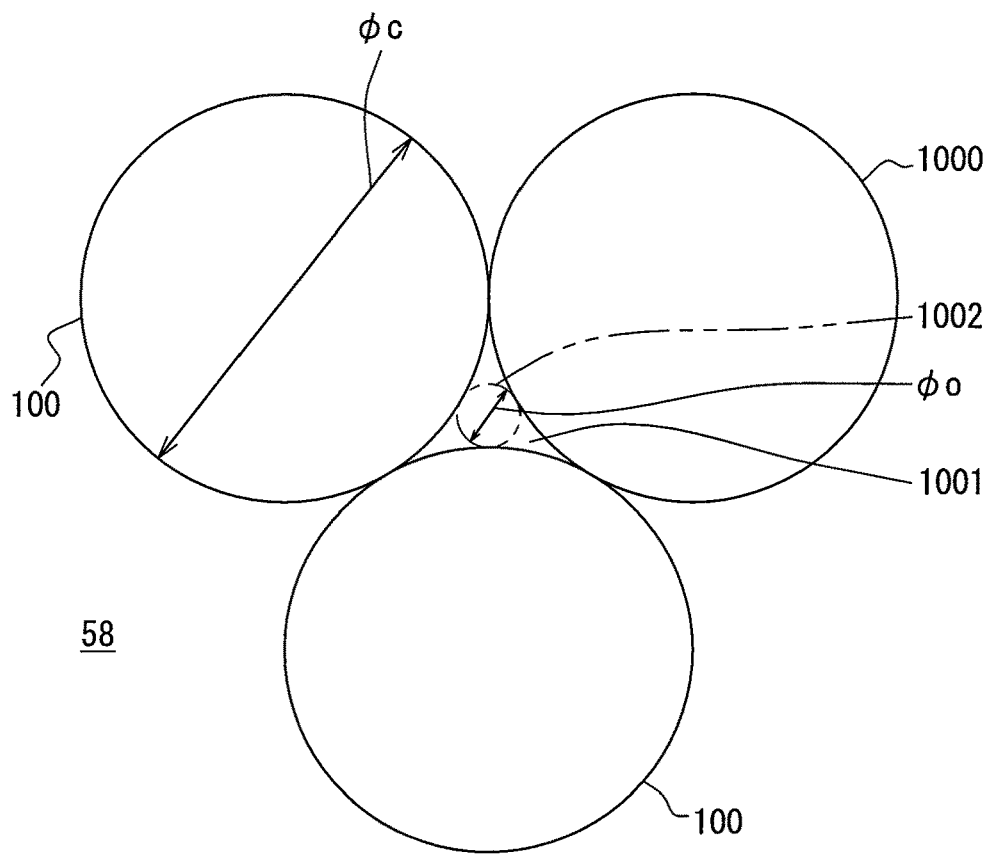
FIG. 11 is a diagram illustrating a schematic diagram showing a detailed configuration of a sensor filter in the first embodiment.

According to the first embodiment, in which an arrangement of each component is explained by utilizing the projection view, the body opening portion 53a as a circle contour shape, the cover window 56f, and a rectangular contour 58ae as the filtering area R are arranged in such a manner that each center of the body opening portion 53a, the cover window 56f, and the rectangular contour 58ae is substantially aligned, as shown in FIG. 10. In the first embodiment, the diameter A of the circle contour of the body opening portion 53a, the diameter B of the circle contour of the cover window 56f, and the minimum distance C (minimum distance in the radial direction) of the rectangular contour 58ae of the filter peripheral part 58a in the filtering area R satisfy the following formula 1, as shown in FIG. 10.

$$A < B < C \quad \text{(Formula 1)}$$

The sensor filter 58 filters the intake air flowing into the body recess 53 through the cover window 56f and the body opening portion 53a from the intake passage 3. A filtering performance of the sensor filter 58 can be achieved. When the filtering performance is determined, a presumption in which a carbon 1000, which is a foreign particle in the intake air and has a minimum diameter among the foreign particles, is adhered on the sensor filter 58 and arranged to contact each other on the sensor filter 58 only with a gap 1001, is considered. In such presumption, if for example the minimum diameter φc is about 0.003 µm, in the gap 1001 the maximum diameter of an inscribed circle 1002 inside three carbons 1000 is about 0.0046 µm. This figure 0.0046 µm is larger than 0.0004 µm, which designates a minimum diameter of a gap for passing the water vapor in the intake air for the humidity detection. A mesh (namely, gap size for passing the water vapor) of the sensor filter 58 for determining the filter performance is set to between for example 0.001-0.003 µm such that the water vapor in the intake air can be passed through the gap 1001 and through the sensor filter 58. In consideration with the mesh, the thickness between both of the surfaces 58b, 58c of the sensor filter 58 is set to for example, about 0.1 mm.

Effects

The effects in the first embodiment will be explained below.

According to the first embodiment, the sensor body 52 provided with the body recess 53 which opens at an body opening portion 53a, is covered by the sensor cover 56 provided with the cover window 56f penetrating between the intake passage 3 and the body opening portion 53a. In such configuration, the sensor filter 58 is provided with the filter peripheral part 58a extending along the virtual plane S. The body opening portion 53a and the cover window 56f are positioned in the filtering area R positioned on an inner side with respect to the contour 58ae of the filter peripheral part 58a in the projection view with respect to the virtual plane S. The filter peripheral part 58a positions between the sensor body 52 and the sensor cover 56 and contacts the sensor body 52 and the sensor cover 56, such that a shape of the sensor filter 58 extending along the virtual plane S can be maintained and the sensor filter 58 is prevented to remove from between the sensor body 52 and the sensor cover 56.

According to the first embodiment, the filter peripheral part 58a of the sensor filter 58, which extending along the virtual plane S, are interposed between the sensor body 52 and the sensor cover 56. Since the filter peripheral part 58a positions between the sensor body 52 and the sensor cover 56 and contacts the sensor body 52 and the sensor cover 56, the sensor filter 58 is prevented to remove from between the sensor body 52 and the sensor cover 56.

According to the first embodiment, in the projection view with respect to the virtual plane S, the body opening portion 53a is positioned in the cover window 56f within the filtering area R. The air flowing through the cover window 56f and the sensor filter 58 from the intake passage 3 introduces into the body recess 53 from the body opening portion 53a without being blocked by the sensor body 52 around the body opening portion 53a. The air from the intake passage 3 easily reaches to the sensor element 54 in the body recess 53. Since the sensor filter 58 extending along the virtual plane S is provided between the sensor body 52 and the sensor cover 56, the sensor filter 58 is positioned near to the sensor element 54 in the body recess 53. As a result, since an inner volume of the body recess 53 is small, a time of the air flowing from the intake passage 3 to the sensor element 54 can be shortened. Accordingly, since the air easily reaches the sensor element 54 and the air flowing time to the sensor element 54 is also minimized, the detection response of the sensor element 54 can be enhanced.

According to the first embodiment, air including the foreign particle in the intake passage of the internal combustion engine is filtered by the sensor filter 58. So, the foreign particle is removed, before the foreign particle reaches the body recess 53. The sensor element 54 in the body recess 53 is prevented from the damage of the foreign particle directly to the sensor element 53. Since the sensor filter 53 is strongly held between the sensor body 52 and the sensor cover 56, the sensor filter 53 is prevented to be removed and then to be flowed from the intake passage 3 to the cylinder in the downstream side.

Second Embodiment

The second embodiment is a modification of the first embodiment.

Figure 12:
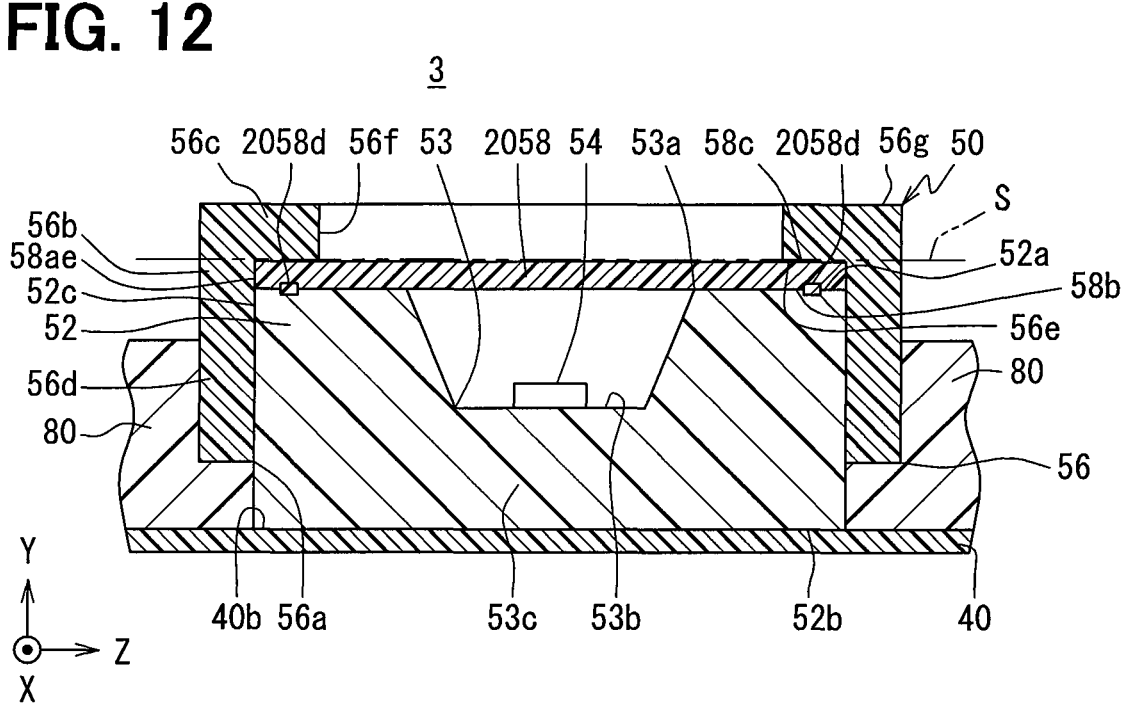
FIG. 12 is a diagram illustrating a cross-sectional view showing the sensor unit in a second embodiment.
Figure 13:
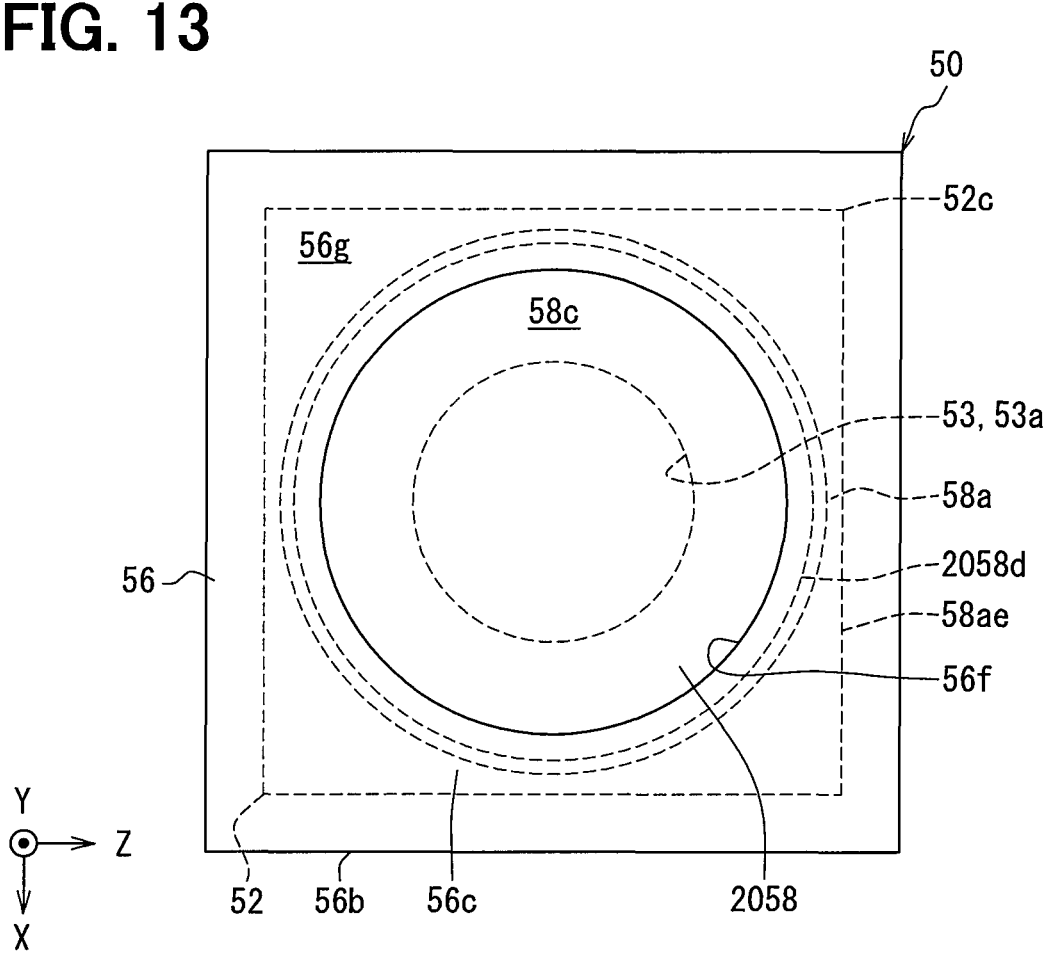
FIG. 13 is a diagram illustrating a plan view showing the sensor unit in the second embodiment.

As shown in FIG. 12, in a sensor filter 2058 according to the second embodiment, one surface 58b of the filter peripheral part 58a is connected on the opposite surface 52a of the sensor body 52 with respect to the mounting surface 40b in a contacting state by welded or bonded, etc. The filter peripheral part 58a, as shown in FIGS. 12 and 13, is provided with a body connecting portion 2058d on the side of the sensor body 52, and the body connecting portion 2058d is formed as a continuous circle belt shape having a substantially same width in a planar view in Y direction.

The filter peripheral part 58a in the sensor filter 2058 is provided with an opposite surface 58c positioned in an opposite side of the sensor body 52, which surface contacts on the inner surface 56e of the bottom wall portion 56c such that the filter peripheral part 58a is interposed between the sensor body 52 and the sensor cover 56. In the sensor filter 2058 connected to the sensor body 52, a slight deformation of the filter peripheral part 58a held between the sensor body 52 and the bottom wall portion 56c may be occurred due to a microscopically roughness of each of the sensor body 52 and the bottom wall portion 56c contacting the filter peripheral part 58a. A specification (for example, dimension and material) for the sensor filter 2058, the sensor body 52, and the bottom wall portion 56c is determined in such a manner that the slight deformation is targeted within a permissible range not hindering a filtering performance of the sensor filter 58.

Figure 14:
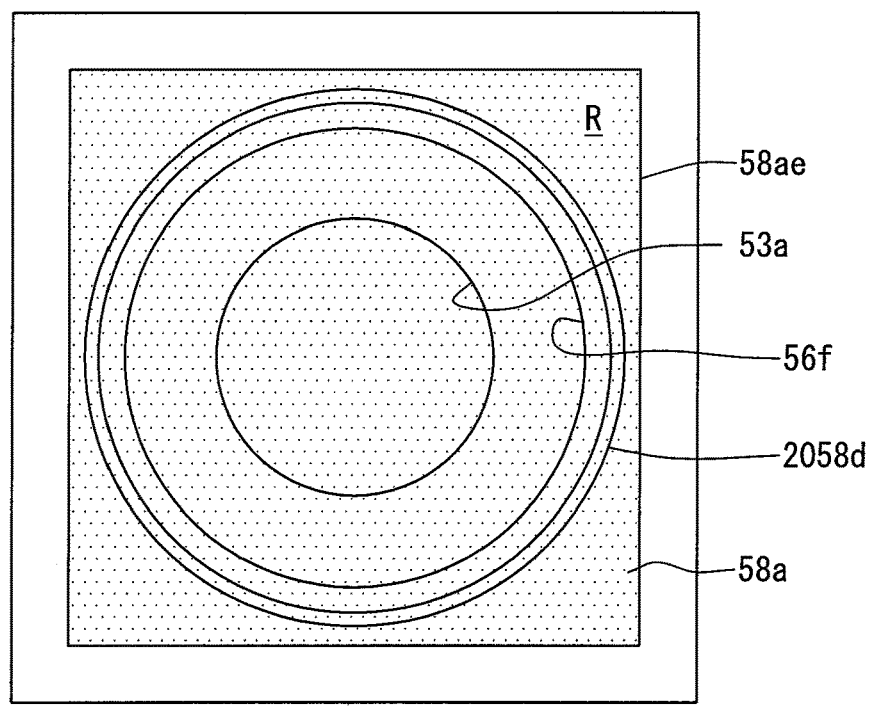
FIG. 14 is a diagram illustrating a schematic diagram showing a detailed configuration of the sensor unit in the second embodiment.

As shown in FIG. 14, under the same definition of the filtering area R in the first embodiment, in the projection view in Y direction with respect to the virtual plane S, the cover window 56f, the body opening portion 53a, and the body connecting portion 2058d are positioned in the filtering area R. In the projection view in Y direction with respect to the virtual plane S, the body connecting portion 2058d is positioned outside of the contour of the body opening portion 53a and outside of the contour of the cover window 56f within the filtering area R. Namely, in the projection view in Y direction with respect to the virtual plane S, the body connecting portion 2058d is positioned between the rectangular contour 58ae of the filter peripheral part 58a and the contour of the cover window 56f.

Figure 15:
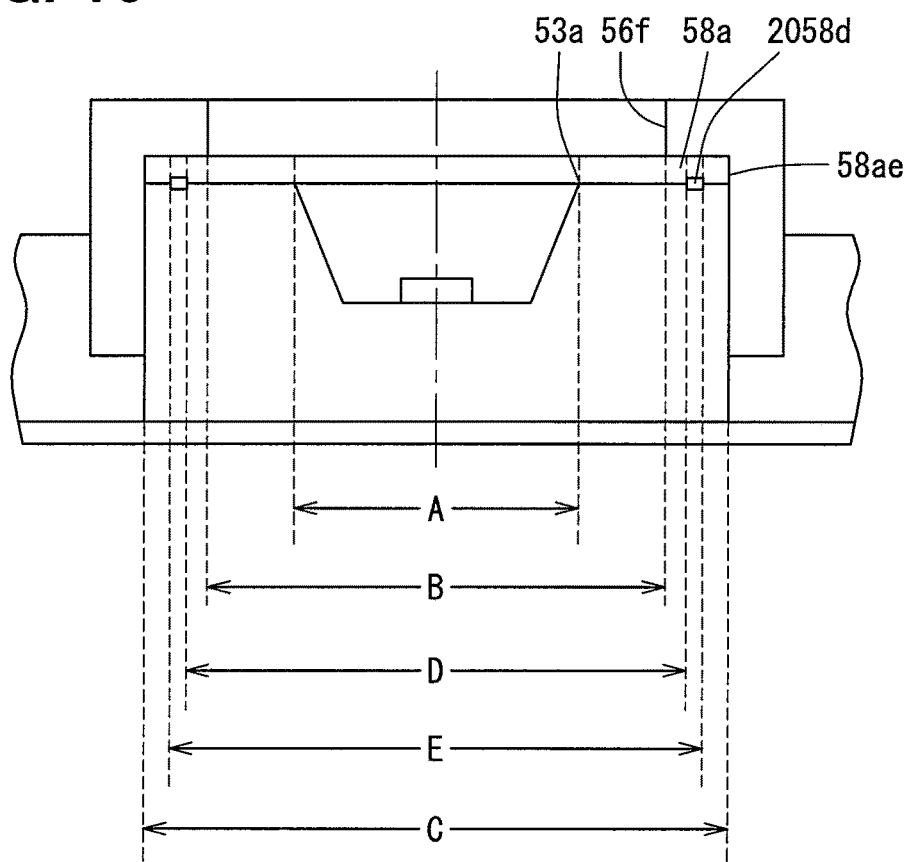
FIG. 15 is a diagram illustrating a schematic diagram showing a detailed configuration of a sensor filter in the second embodiment.

According to the second embodiment, the body connecting portion 2058d as circle belt shape, the body opening portion 53a as a circle contour shape, the cover window 56f, and a rectangular contour 58ae as the filtering area R are arranged in such a manner that each center of the body connecting portion 2058d, the body opening portion 53a, the cover window 56f, and a rectangular contour 58ae is substantially aligned, as shown in FIG. 15. In the second embodiment, the diameter D of the inner side of the body connecting portion 2058d, the diameter E of the outer side of the body connecting portion 2058d, the diameter A of the circle contour of the body opening portion 53a, the diameter B of the circle contour of the cover window 56f, and the minimum distance C (minimum distance in the radial direction) of the rectangular contour 58ae of the filter peripheral part 58a in the filtering area R satisfy the following formula 2, as shown in FIG. 15.

$$A<B<D<E<C \qquad \text{(Formula 2)}$$

According to the second embodiment, the body connecting portion 2058d in the filter peripheral part 58a, connected to the sensor body 52, is positioned within the filtering area R in the projection view with respect to the virtual plane S. The filter peripheral part 58a positions between the sensor body 52 and the sensor cover 56 and contacts the sensor body 52 and the sensor cover 56, such that a shape of the sensor filter 2058 extending along the virtual plane S can be maintained and the sensor filter 58 is prevented to remove from between the sensor body 52 and the sensor cover 56. The removal of the sensor filter 2058 and the deformation of the sensor filter 2058 are suppressed for a long time. According to the second embodiment, the filter peripheral part 58a is joined to the sensor body 52 at the body connecting portion 2058d, and furthermore the filter peripheral part 58a is held between the sensor body 52 and the sensor cover 56, such that the removal of the sensor filter 2058 and the deformation of the sensor filter 2058 are highly suppressed.

According to the second embodiment, within the filtering area R in the projection view with respect to the virtual plane S, the body opening portion 53a is positioned inside of the cover window 56f, and the body connecting portion 2058d is positioned outside of the cover window 56f. A space between the contour of the filter peripheral part 58a and the contour of the cover window 56f is effectively utilized such that the space for the width of the body connecting portion 2058d can be widened. The joined area at the body connecting portion 2058d connecting the filter peripheral portion 58a to the sensor body 52 can be larger. So, the joined strength between the filter peripheral portion 58a and the sensor body 52 is enhanced and the removal of the sensor filter 2058 is prevented.

Third Embodiment

The third embodiment is a modification of the second embodiment.

Figure 16:
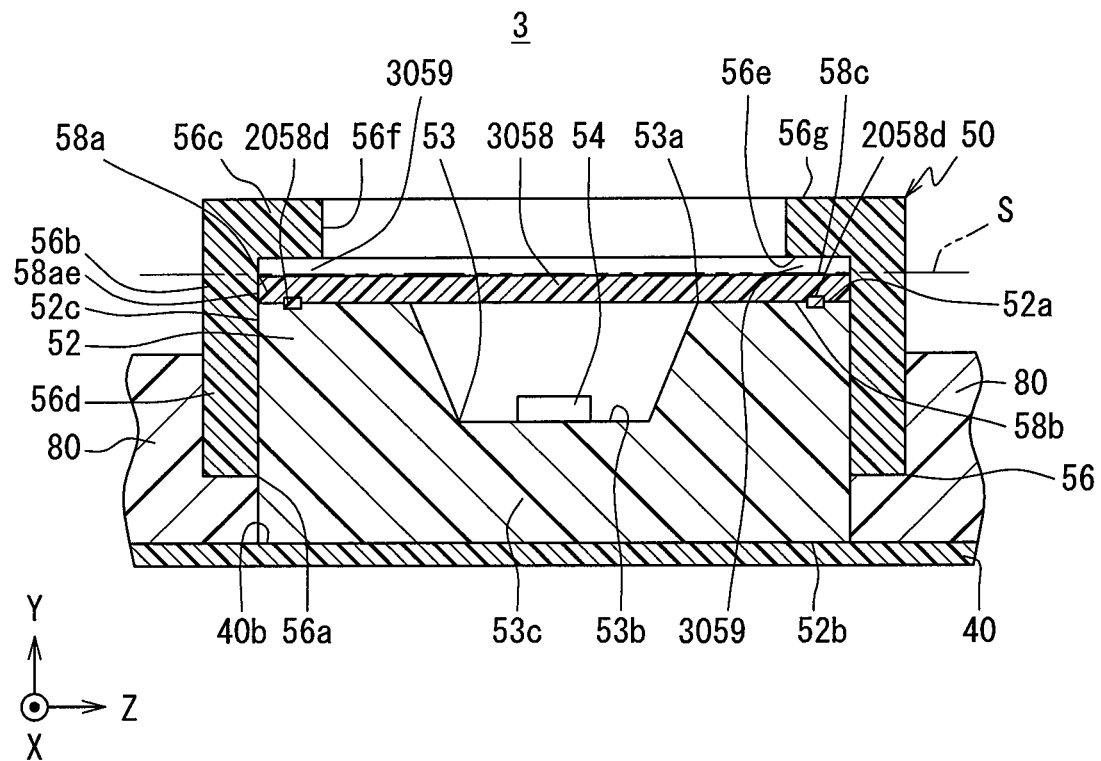
FIG. 16 is a diagram illustrating a cross-sectional view showing the sensor unit in a third embodiment.

As shown in FIG. 16, the opposite surface 58c of the filter peripheral part 58a in the opposite side of the sensor unit 52 is separated from the inner surface 56e of the bottom wall portion 56c in the sensor cover 56 with a gap. A cover space portion 3059 is formed between the filter peripheral part 58a and the bottom wall portion 56c in Y direction. One surface 58b of the filter peripheral part 58a is joined to the opposite surface 52a of the sensor body 52 with respect to the mounting surface 40b in a surface contacting state.

In the sensor filter 3058 according to the third embodiment, since the cover space portion 3059 is formed between the filter peripheral part 58a and the sensor cover 56, a design freedom, such as measurement or tolerance, etc. is enhanced. A yield rate for manufacturing the sensor unit 50 is reduced.

Fourth Embodiment

The fourth embodiment is a modification of the first embodiment.

Figure 17:
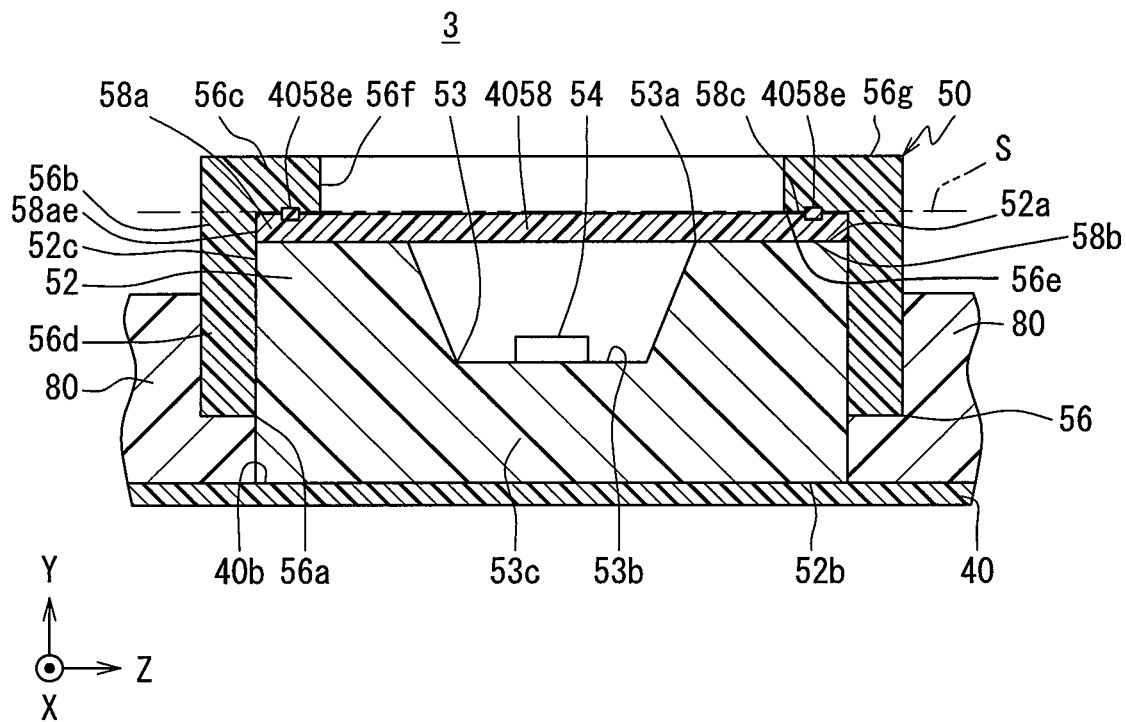
FIG. 17 is a diagram illustrating a cross-sectional view showing the sensor unit in a fourth embodiment.
Figure 18:
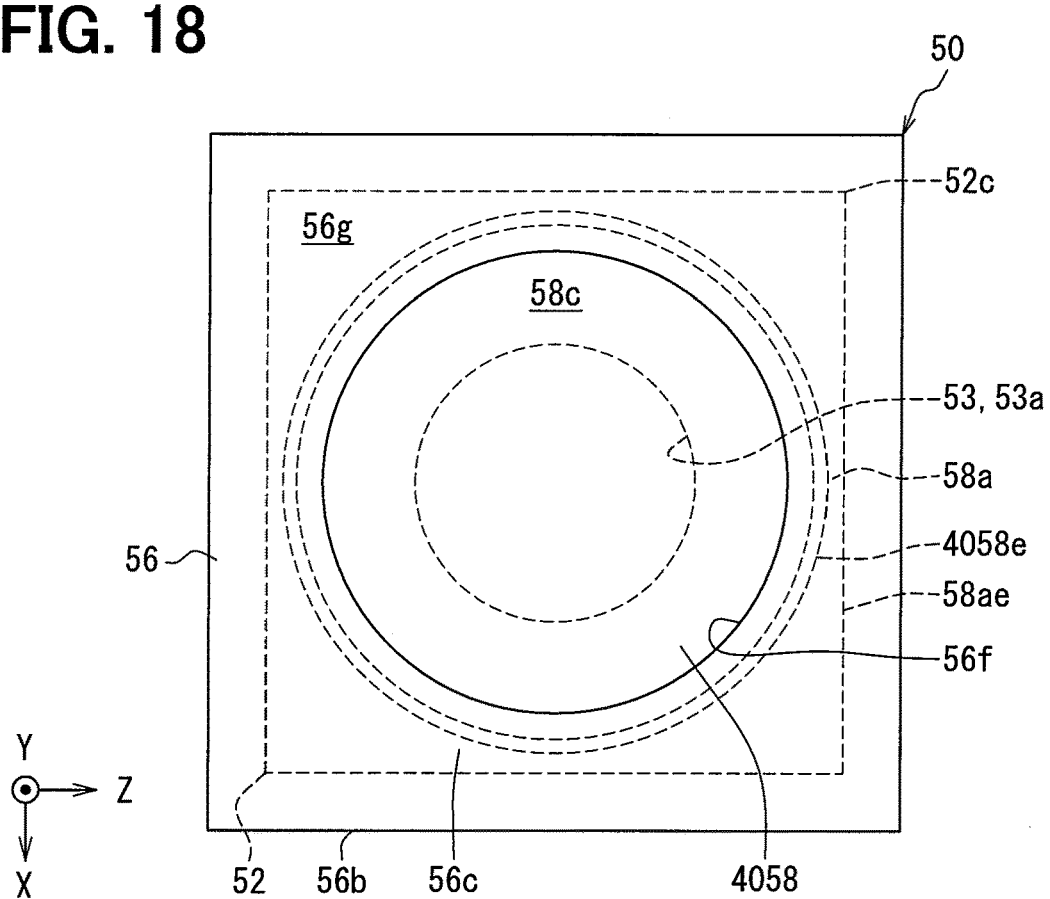
FIG. 18 is a diagram illustrating a plan view showing the sensor unit in the fourth embodiment.

As shown in FIG. 17, in a sensor filter 4058 according to the fourth embodiment, one surface 58c of the filter peripheral part 58a opposite to the sensor body 52 is connected to the inner surface 56e of the bottom wall portion 56c in the sensor cover 56 in a surface contacting state by welded or bonded, etc. The filter peripheral part 58a, as shown in FIGS. 17 and 18, is provided with a cover connecting portion 4058e on the side of the sensor cover 56, and the cover connecting portion 4058e is formed as a circle belt shape having a substantially same width in a planar view in Y direction.

The filter peripheral part 58a in the sensor filter 4058 is provided with one surface 58b surface-contacts on the opposite surface 52a of the sensor body 52 with respect to the mounting surface 40b such that the filter peripheral part 58a is interposed between the sensor body 52 and the sensor cover 56. In the sensor filter 4058 connected to the sensor cover 56, a slight deformation of the filter peripheral part 58a held between the sensor body 52 and the bottom wall portion 56c may be occurred due to a microscopically roughness of each of the sensor body 52 and the bottom wall portion 56c contacting the filter peripheral part 58a. A specification (for example, dimension and material) for the sensor filter 4058, the sensor body 52, and the bottom wall portion 56c is determined in such a manner that the slight deformation is targeted within a permissible range not hindering a filtering performance of the sensor filter 58.

Figure 19:
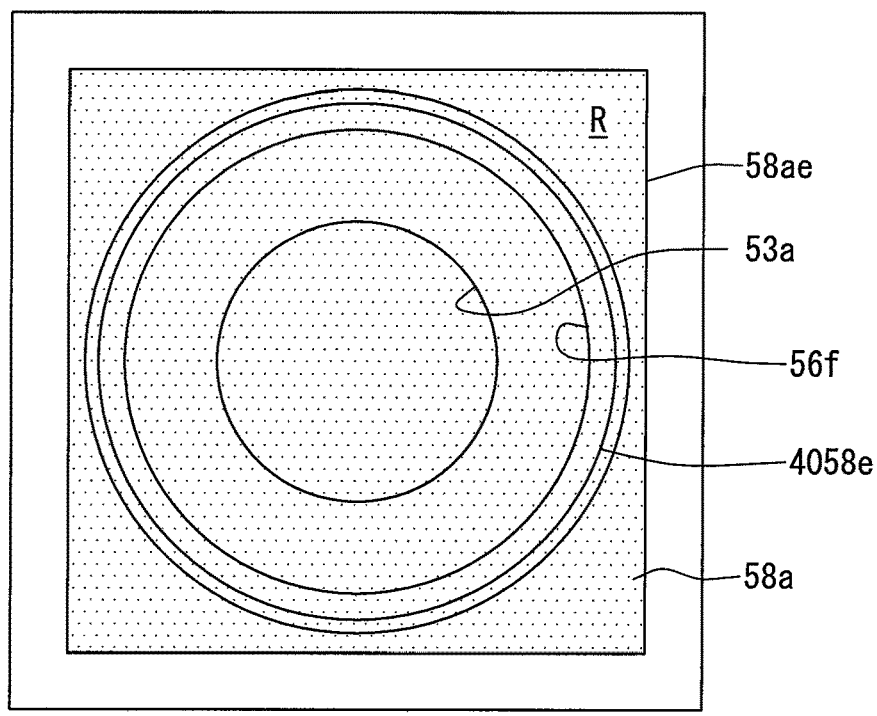
FIG. 19 is a diagram illustrating a schematic diagram showing a detailed configuration of the sensor unit in the fourth embodiment.

As shown in FIG. 19, under the same definition of the filtering area R in the first embodiment, in the projection view in Y direction with respect to the virtual plane S, the cover window 56f, the body opening portion 53a, and the cover connecting portion 4058e are positioned within the filtering area R. In the projection view in Y direction with respect to the virtual plane S, the cover connecting portion 4058e is positioned outside of the contour of the body opening portion 53a and outside of the contour of the cover window 56f within the filtering area R. Namely, in the projection view in Y direction with respect to the virtual plane S, the cover connecting portion 4058e is positioned between the rectangular contour 58ae of the filter peripheral part 58a and the contour of the cover window 56f.

Figure 20:
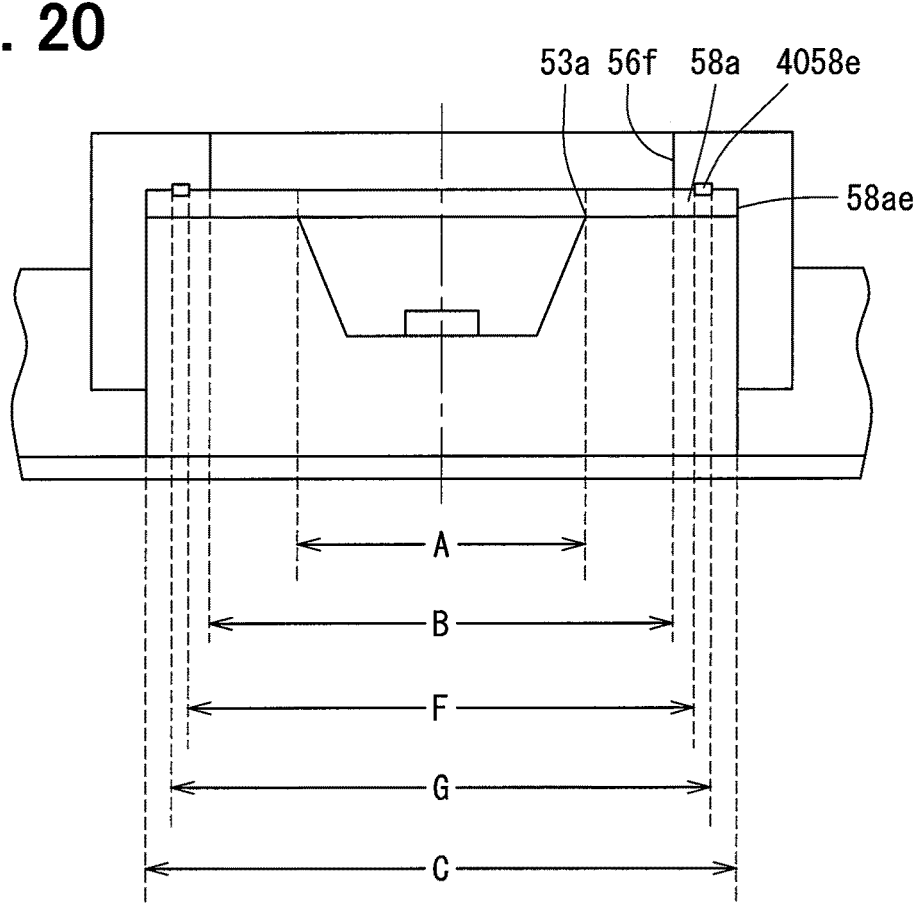
FIG. 20 is a diagram illustrating a schematic diagram showing a detailed configuration of a sensor filter in the fourth embodiment.

According to the fourth embodiment, the cover connecting portion 4058e as circle belt shape, the body opening portion 53a as a circle contour shape, the cover window 56f, and a rectangular contour 58ae as the filtering area R are arranged in such a manner that each center of the cover connecting portion 4058e, the body opening portion 53a, the cover window 56f, and a rectangular contour 58ae is substantially aligned, as shown in FIG. 15. In the second embodiment, the diameter F of the inner side of the cover connecting portion 4058e, the diameter G of the outer side of the cover connecting portion 4058e, the diameter A of the circle contour of the body opening portion 53a, the diameter B of the circle contour of the cover window 56f, and the minimum distance C (minimum distance in the radial direction) of the rectangular contour 58ae of the filter peripheral part 58a in the filtering area R satisfy the following formula 3, as shown in FIG. 20.

$$A<B<F<G<C \quad \text{(Formula 3)}$$

According to the fourth embodiment, the cover connecting portion 4058e in the filter peripheral part 58a, connected to the sensor cover 56, is positioned within the filtering area R in the projection view with respect to the virtual plane S. The filter peripheral part 58a positions between the sensor body 52 and the sensor cover 56 and contacts the sensor body 52 and the sensor cover 56, such that a shape of the sensor filter 4058 extending along the virtual plane S can be maintained and the sensor filter 58 is prevented to remove from between the sensor body 52 and the sensor cover 56. The removal of the sensor filter 2058 and the deformation of the sensor filter 4058 are suppressed for long time. According to the second embodiment, the filter peripheral part 58a is joined to the sensor body 52 at the cover connecting portion 4058e, and furthermore the filter peripheral part 58a is held between the sensor body 52 and the sensor cover 56, such that the removal of the sensor filter 4058 and the deformation of the sensor filter 4058 are highly suppressed.

According to the fourth embodiment, within the filtering area R in the projection view with respect to the virtual plane S, the body opening portion 53a is positioned inside of the cover window 56f, and the cover connecting portion 4058e is positioned outside of the cover window 56f. A space between the contour of the filter peripheral part 58a and the contour of the cover window 56f is effectively utilized such that the space for the width of the cover connecting portion 4058e can be widened. The joined area at the cover connecting portion 4058e connecting the filter peripheral portion 58a to the sensor body 52 can be larger. So, the joined strength between the filter peripheral portion 58a and the sensor body 52 is enhanced and the removal of the sensor filter 2058 is prevented.

Firth Embodiment

The fifth embodiment is a modification of the fourth embodiment.

Figure 21:
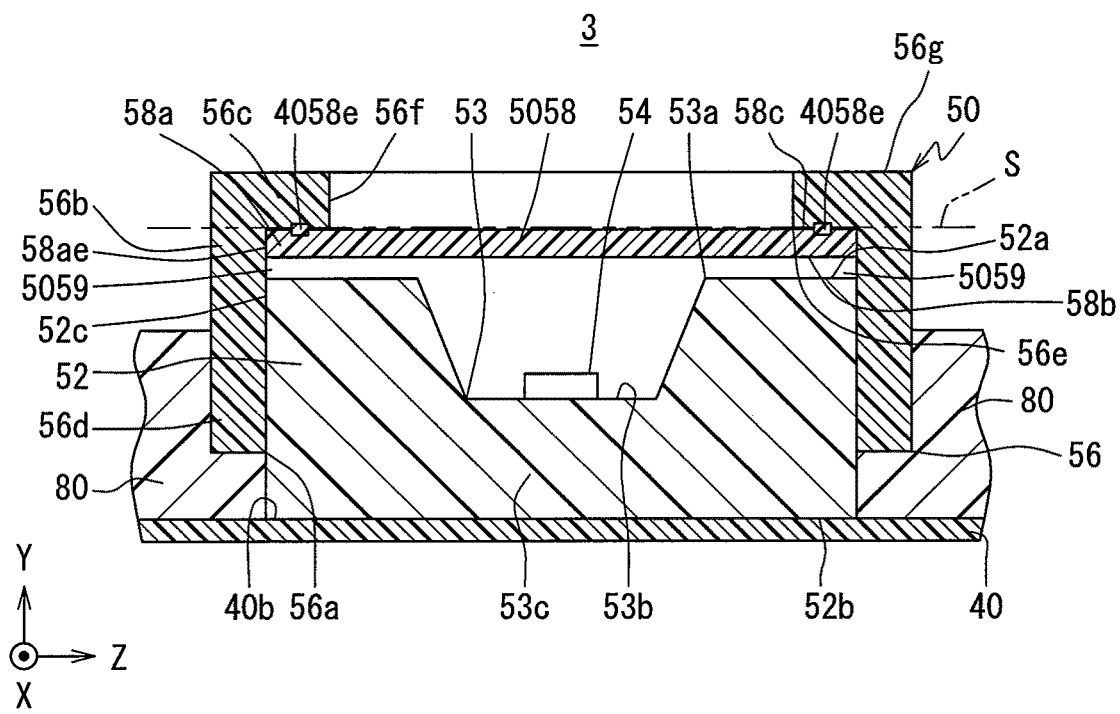
FIG. 21 is a diagram illustrating a cross-sectional view showing the sensor unit in a fifth embodiment.

As shown in FIG. 21, in a sensor filter 5058 according to the fifth embodiment, one surface 58b of the filter peripheral portion 58a is separated from the opposite surface 52a of the sensor body 52 with respect to the mounting surface 40b with a gap. A space portion 5019 is formed in Y direction between the filter peripheral portion 58a and the sensor body 52. In the sensor filter 5058, one surface 58c of the filter peripheral part 58a opposite to the sensor body 52 is connected to the inner surface 56e of the bottom wall portion 56c in the sensor cover 56 in a surface contacting state in the same manner as in the fourth embodiment.

In the sensor filter 5058 according to the fifth embodiment, since the space portion 5019 is formed between the filter peripheral part 58a and the sensor body 52, a design freedom, such as measurement or tolerance, etc. is enhanced. A yield rate for manufacturing the sensor unit 50 is reduced.

Sixth Embodiment

The sixth embodiment is a modification of the combination of the second embodiment and the fourth embodiment.

Figure 22:
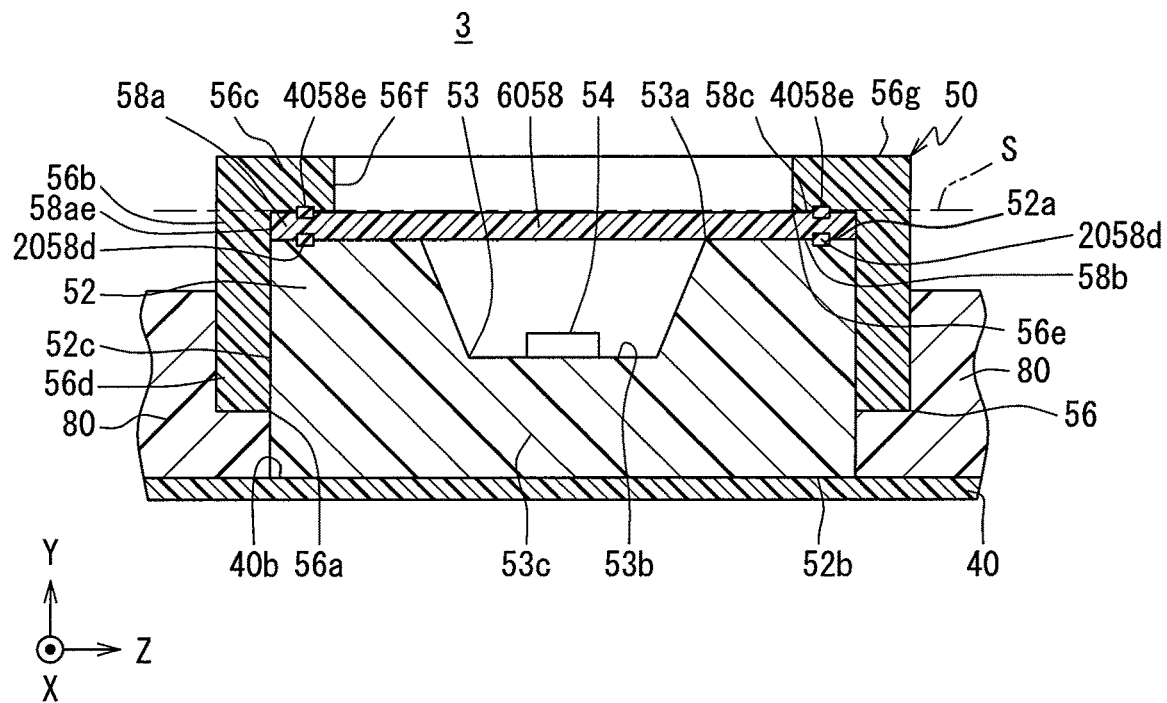
FIG. 22 is a diagram illustrating a cross-sectional view showing the sensor unit in a sixth embodiment.

As shown in FIG. 22, a sensor filter according to the sixth embodiment is connected to the sensor body 52 and the sensor cover 56 in a surface contacting state by welded or bonded, etc. In the sensor filter 6058, the body connecting portion 2058d in the same manner as in the second embodiment and the cover connecting portion 4058e in the same manner as in the fourth embodiment are formed.

Figure 23:
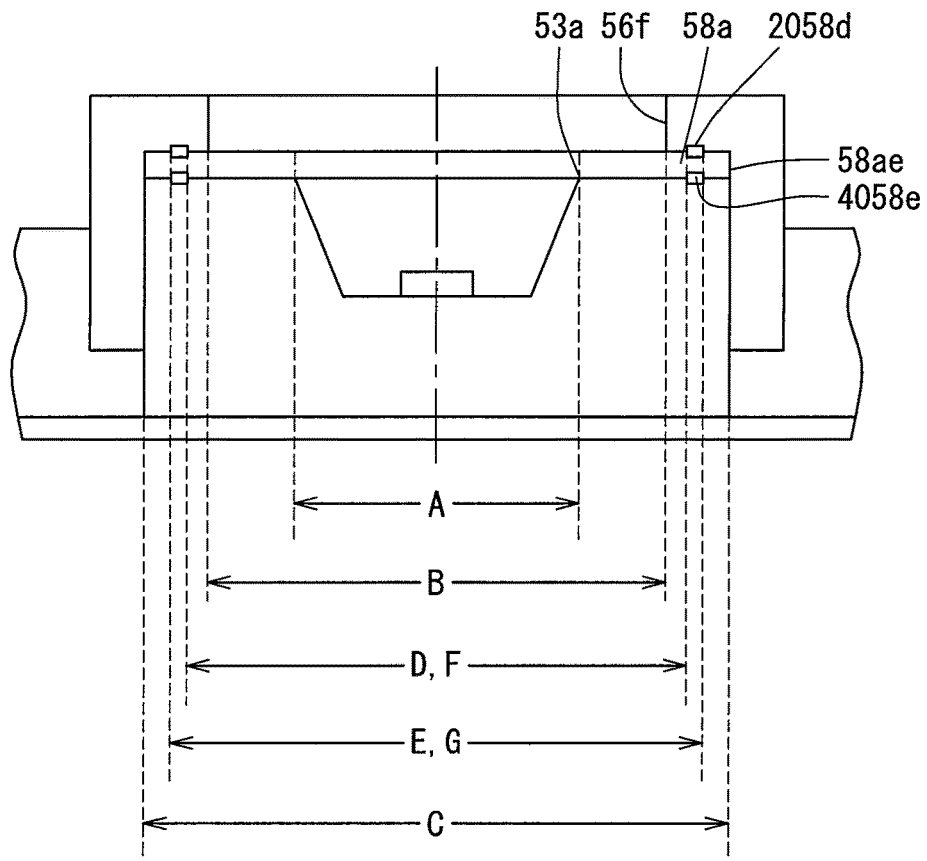
FIG. 23 is a diagram illustrating a schematic diagram showing a detailed configuration of the sensor unit in the sixth embodiment.

Under the same definition of the filtering area R in the first embodiment, a projection view in the same manner as in the second embodiment and a projection view in the same manner as in the fourth embodiment are realized. In the sixth embodiment, as shown in FIG. 23, the diameter D of the inner side of the body connecting portion 2058d is substantially same to the diameter F of the inner side of the cover connecting portion 4058e. The diameter E of the outer side of the body connecting portion 2058d is substantially same to the diameter G of the outer side of the cover connecting portion 4058e.

In the sixth embodiment, the body connecting portion 2058d connected between the filter peripheral portion 58a and the sensor body 52 and the cover connecting portion 4058e connected between the filter peripheral portion 58a and the sensor cover 56 are positioned within the filtering area R in the projection view with respect to the virtual plane S. In the sensor filter extending along the virtual plane S, the connecting state connecting the filter peripheral portion 58a with both the sensor body 52 and the sensor cover 56 can be maintained. In the sixth embodiment, the filter peripheral part 58a is respectively joined to the sensor body 52 at the body connecting portion 2058d and to the sensor cover 56 at the cover connecting portion 4058e, and furthermore the filter peripheral part 58a is held between the sensor body 52 and the sensor cover 56, such that the removal of the sensor filter 4058 and the deformation of the sensor filter 4058 are highly suppressed.

Seventh Embodiment

The seventh embodiment is a modification of the first embodiment.

Figures 24, 25:
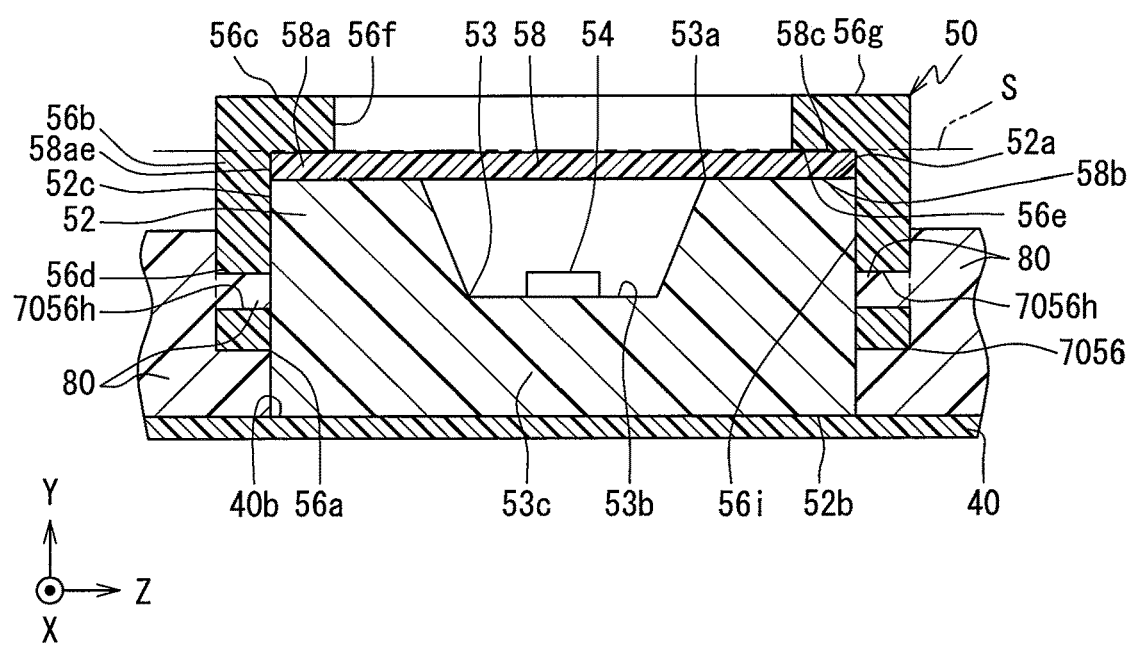
FIG. 24 is a diagram illustrating a cross-sectional view showing the sensor unit in the seventh embodiment.
FIG. 25 is a diagram illustrating a plan view showing the sensor unit in the seventh embodiment.

As shown in FIGS. 24 and 25, a sensor cover 7056 formed as a shape of bottomed cup according to the seventh embodiment, has a through hole 7056h in the peripheral portion 56b. As shown in FIG. 25, one through hole 7056h is formed in each wall of four walls of the cover peripheral portion 56b formed as the rectangular tube shape. The through hole 7056h is penetrated in X direction or Z direction, such that the embedded portion 56d is formed to be embedded into the through hole 7056h by the potting resin 80. The through hole 7056h penetrates the embedded portion 56d at the position between the body opening portion 56a of the cover peripheral portion 56b and the bottom wall portion 56c thereof. The construction of the sensor unit 50, which is not explained in the seventh embodiment, may be replaced by each construction among the second embodiment and the sixth embodiment instead of the construction in the first embodiment.

Figure 26:
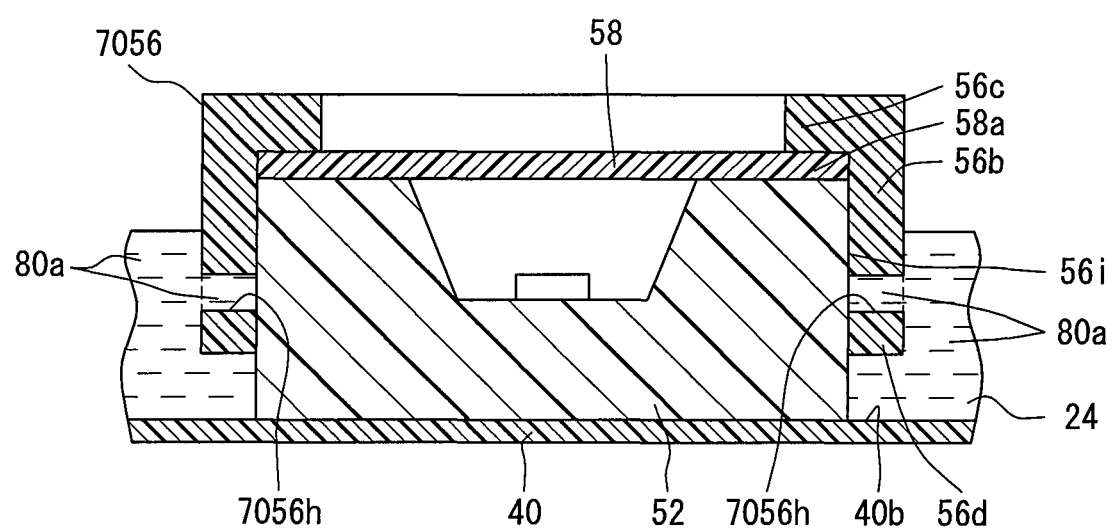
FIG. 26 is a diagram illustrating a schematic diagram showing a method for manufacturing the sensor unit in the seventh embodiment.

In the seventh embodiment, a thermosetting resin 80a as a forming material of the potting resin 80, as shown in FIG. 26, fills into each hole through 7056h 24 in a melting state, and fills into the fitting clearance 56i between the sensor body 52 and the cover peripheral portion 56b, and then is cooled and cured. As shown in FIG. 24, the potting resin 80 is embedded in each through hole 7056h and is formed in the fitting clearance 56i between the sensor body 52 and the cover peripheral portion 56b from the through hole 7056h.

In the sensor cover 7056 formed as a shape of bottomed cup according to the seventh embodiment, the through hole 7056h penetrates the cover peripheral portion 56b at the position between the body opening portion 56a of the cover peripheral portion 56b and the bottom wall portion 56c thereof. Since the thermosetting resin 80a as a forming material of the potting resin 80 in a melting state fills into the through hole 7056h, a floating of the potting resin 80 with respect to the sensor substrate 40 is prevented because of an inner pressure of the potting resin 80. The sensor cover 7056 is fixed at a predetermined position by using the potting resin 80 for covering the circuit elements 72, and a position displacement of the sensor filter 58 provided between the sensor cover 7056 and the sensor body 52 is suppressed. In the seventh embodiment which achieves the above mentioned effects, when the thermosetting resin 80a embeds into the embedded portion 56d in a melting state, a load toward the bottom surface 24a of the recess portion 24 may continue to act on the sensor cover 56 as shown in the first embodiment, or a weight of the sensor cover 7056 may be utilized as the load toward the bottom surface 24a of the recess portion 24a as shown in FIG. 24.

Eighth Embodiment

The eighth embodiment is a modification of the first embodiment.

Figure 27:
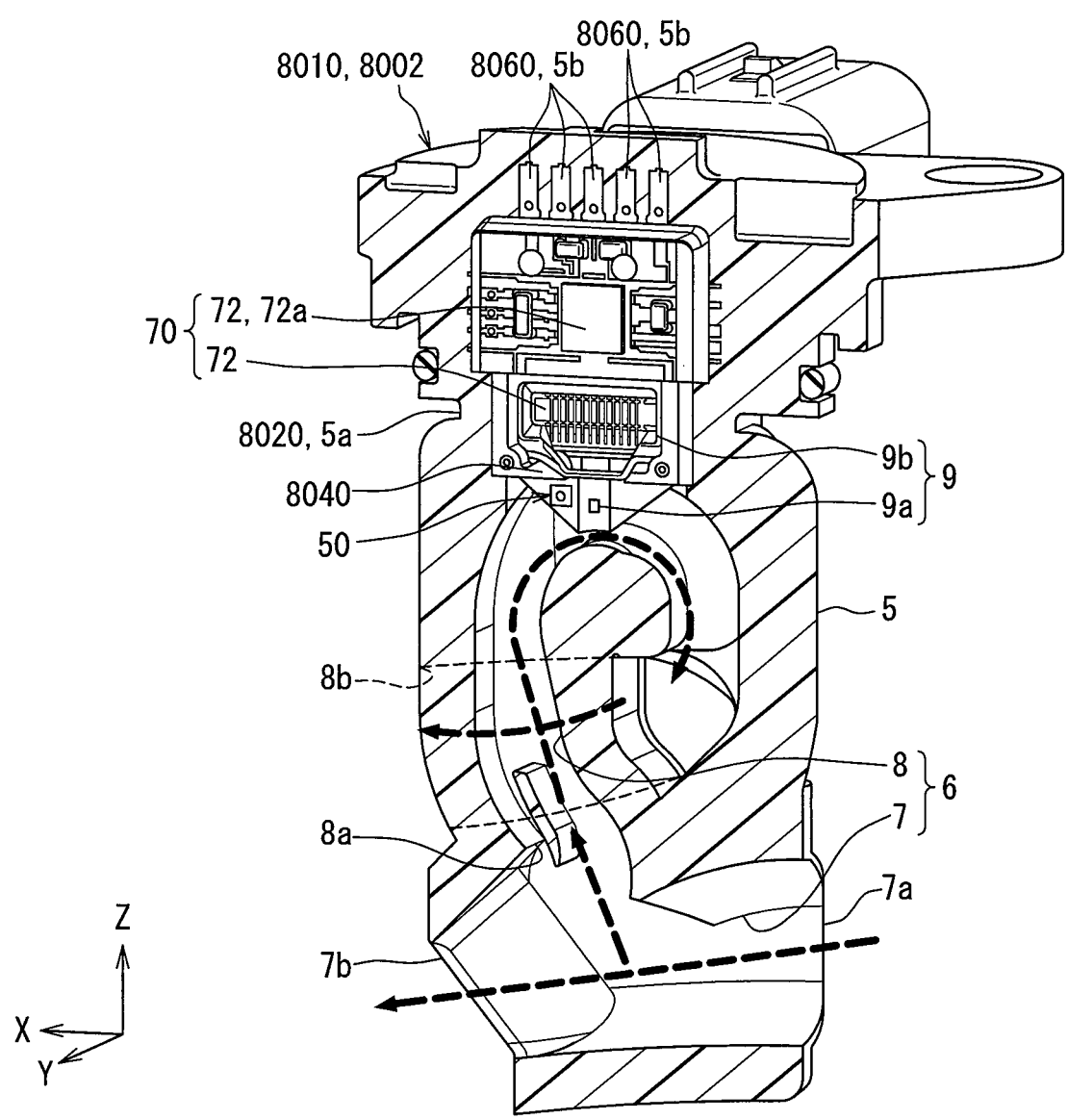
FIG. 27 is a diagram illustrating a perspective and partial cross-sectional view showing the air physical quantity sensor attached to an air flow detection unit in the eighth embodiment.

As shown in FIG. 27, the air physical quantity sensor 8010 according to the eighth embodiment is constructed integrally with the air flow detection unit 8002. The air physical quantity sensor 8010 is provided with the sensor unit 50 exposed to the second passage 8 in the bypass passage 6, in which a part of the intake air from the intake passage 3 flows.

The air physical quantity sensor 8010 includes a sensor case 8020 shared with the detection portion 5a of the flow detection body 5, and plural terminals 8060 shared with plural terminals 5b of the flow detection body 5. In the air physical quantity sensor 8010, the sensor unit 50 and the circuit module 70 are mounted on a sensor substrate 8040 together with the sensor element 9a and the circuit module 9b. Regarding the quantity relating to the intake air flowing in the bypass passage 6, the amount of the flow different from the flow having the humidity detected by the sensor element 54 of the sensor unit 50 is detected by another sensor element 9a mounted on the sensor substrate 8040 for supporting the sensor body 52 of the sensor unit 50. The sensor filter 58 of the sensor unit 50 filters a part of the intake air flowing into the recess portion 53 through the cover window 56f and the body opening portion 53a from the bypass passage 6.

Regarding the construction of the sensor unit 50, each of the construction thereof according to the second to the seventh embodiments may be applied instead of the construction in the first embodiment. In FIG. 27, the illustration regarding each component of the sensor unit 50 is omitted.

In the eighth embodiment, even if the foreign particle is easily mixed in the intake passage 3 of the internal combustion 1, the foreign particle is prevented from entering in the bypass passage 6, according to separation of the intake air from the intake passage 3. The sensor element 54 in the body recess 53 is prevented the foreign particle from directly hitting the sensor element 54, and the removal of the sensor filter 2058 and the deformation of the sensor filter 2058 are highly suppressed, and finally the filtering performance is increased.

In the eighth embodiment, another sensor element 9a for detecting an air quantity different from the air quantity detected by the sensor elements 54, is mounted on the sensor substrate 8040, and the sensor body 52 is supported on the sensor substrate 40. The circuit modules 70, 9b are shared, and the adjustment of the detection value by using the output signal from plural sensor elements 54, 9a is realized, and the sensor unit 50 is downsized.

Other Embodiments

The combination of the above mentioned embodiments may be applied, if the combination would be reasonable.

Figure 28:
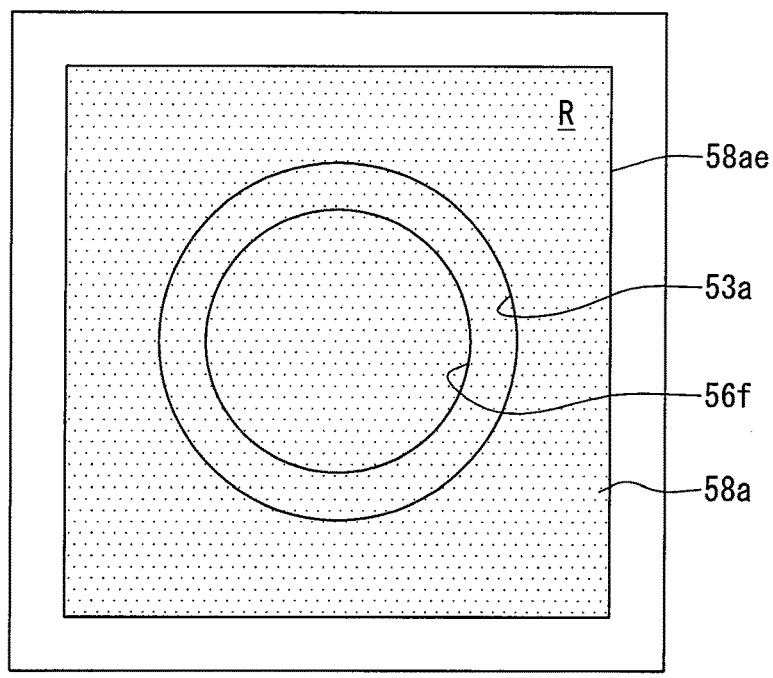
FIG. 28 is a diagram illustrating a schematic diagram showing a modification 1 of the sensor unit relating to FIG. 9.
Figure 29:
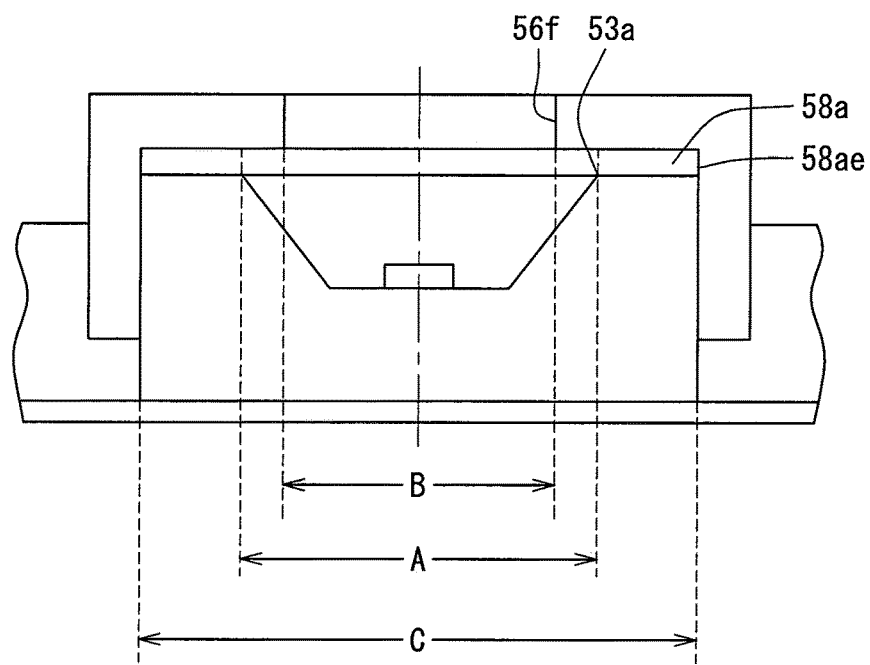
FIG. 29 is a diagram illustrating a schematic diagram showing a modification 1 of the sensor unit relating to FIG. 10.
Figure 30:
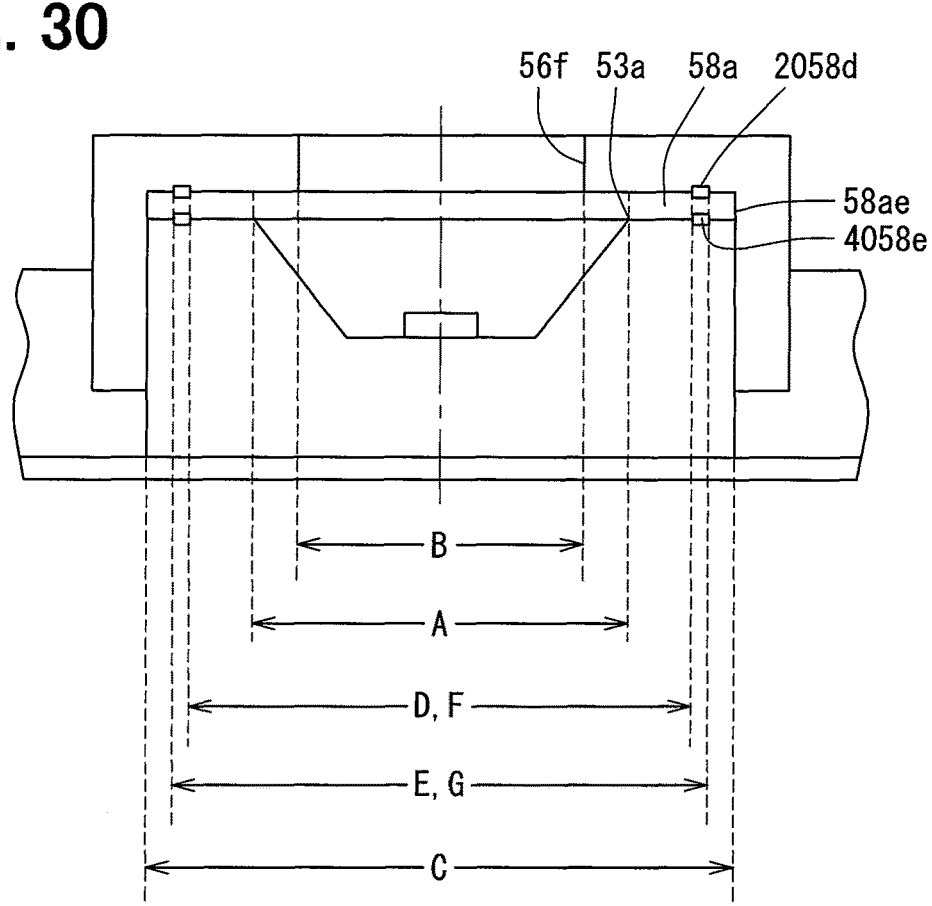
FIG. 30 is a diagram illustrating a schematic diagram showing a modification 1 of the sensor unit relating to FIG. 23.
Figure 31:
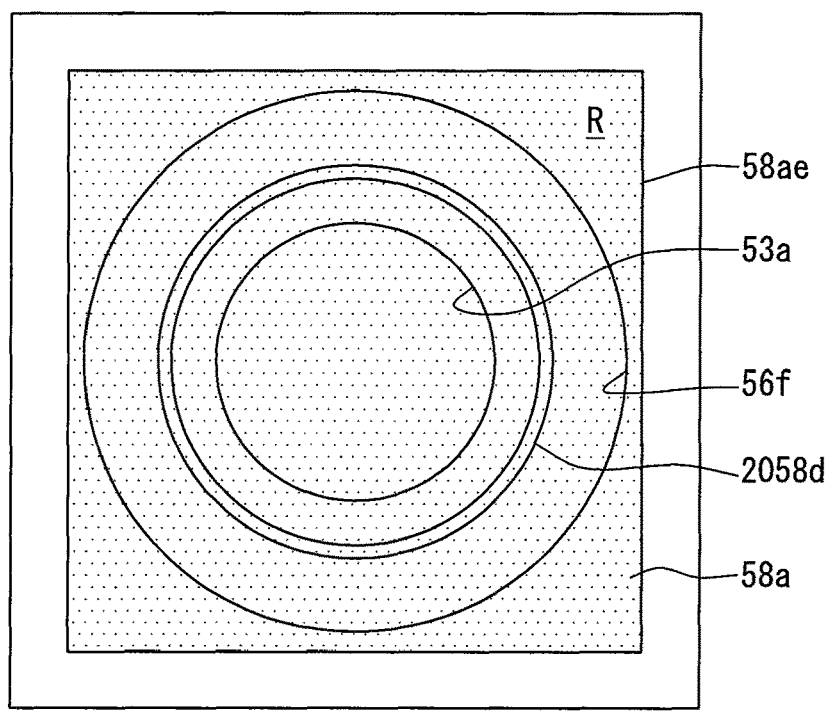
FIG. 31 is a diagram illustrating a schematic diagram showing a modification 2 of the sensor unit relating to FIG. 14.

In the modification 1 relating to the first to the eighth embodiments, in the projection view in Y direction with respect to the virtual plane S, the cover window 56*f* is positioned in an inner side with respect to the contour 58 of the body opening portion 53*a* within the filtering area R as shown in FIG. 28. In the modification 1 relating to the first, the seventh, and the eighth embodiments, as shown in FIG. 29, the following formula 4 is satisfied. In the modification 1 relating to the second, the third, and the sixth embodiments, as shown in FIG. 30, the following formula 5 is satisfied. In the modification 1 relating to the fourth to the sixth embodiments, as shown in FIG. 31, the following formula 6 is satisfied. FIGS. 28 and 29 show the modification 1 relating to the first embodiment, FIG. 30 shows the modification 1 relating to the sixth embodiment.

$$B<A<C \quad \text{(Formula 4)}$$

$$B<A<D<E<C \quad \text{(Formula 5)}$$

$$B<A<F<G<C \quad \text{(Formula 6)}$$

Figure 32:
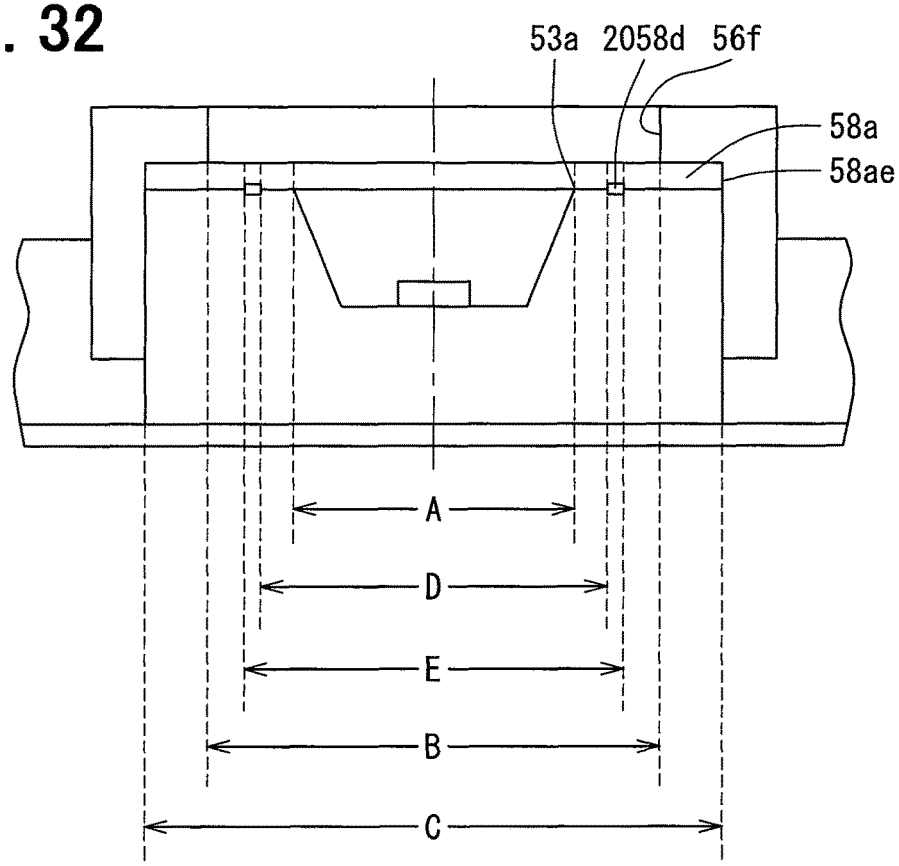
FIG. 32 is a diagram illustrating a schematic diagram showing a modification 2 of the sensor unit relating to FIG. 15.

In the second modification relating to the second, the third, and the sixth embodiments, in the projection view in Y direction with respect to the virtual plane S, the body connecting portion 2058*d* may be positioned in an outer side with respect to the contour 58 of the body opening portion 53*a* within the filtering area R, as shown in FIG. 31. In the projection view in Y direction with respect to the virtual plane S, the body connecting portion 2058*d* may be positioned between the contour of the body opening portion 53*a* and the contour of the cover window 56*f*. In the modification 2, as shown in FIG. 32, the following formula 7 is satisfied. In the modification 2, a space between the contour of the body opening portion 53*a* and the contour of the cover window 56*f* is effectively utilized such that the space for the width of the body connecting portion 2058*d* can be widened. So, the joined strength between the filter peripheral portion 58*a* and the sensor body 52 is enhanced and the removal of the sensor filters 2058, 6058 is prevented. FIGS. 31, 32 show the modification 2 relating to the second embodiment.

$$A<D<E<B<C \quad \text{(Formula 7)}$$

In a modification 3 relating to the sixth embodiment, the inner diameter D of the body connecting portion 2058*d* may be different from the inner diameter F of the cover connecting portion 4058*e*. In a modification 4 relating to the sixth embodiment, the outer diameter E of the body connecting portion 2058*d* may be different from the outer diameter G of the cover connecting portion 4058*e*.

Figure 33:
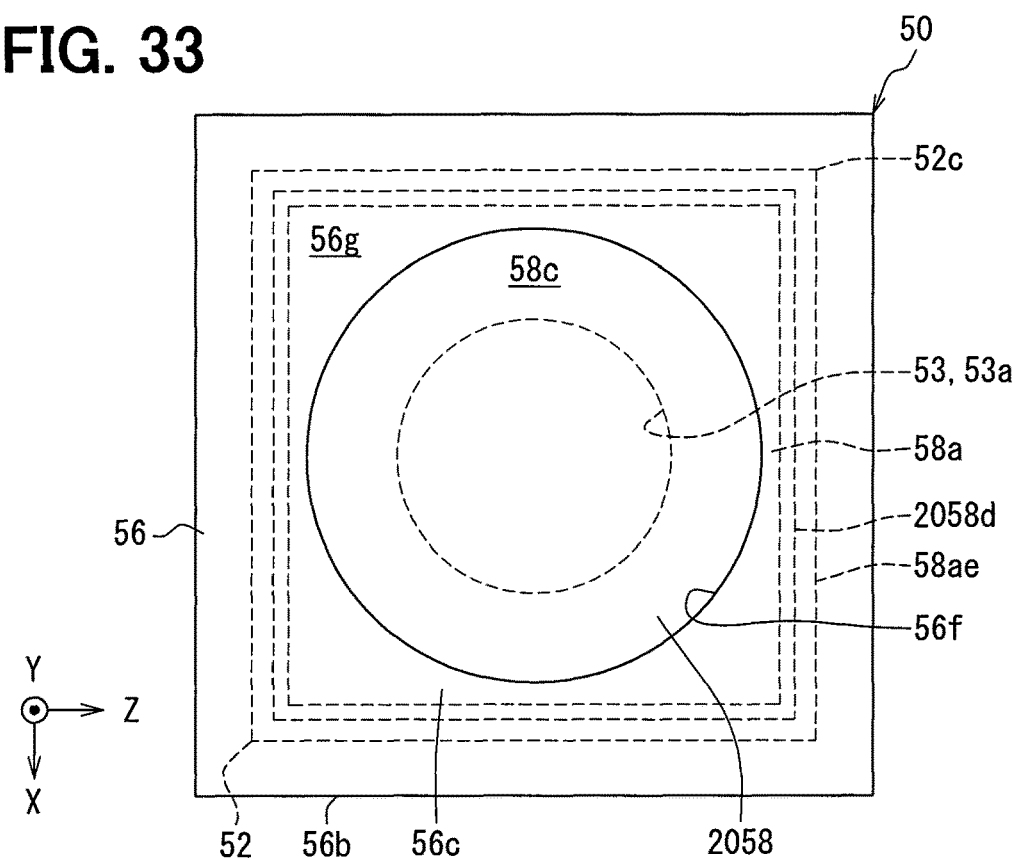
FIG. 33 is a diagram illustrating a plan view showing a modification 5 of the sensor unit relating to FIG. 13.
Figure 34:
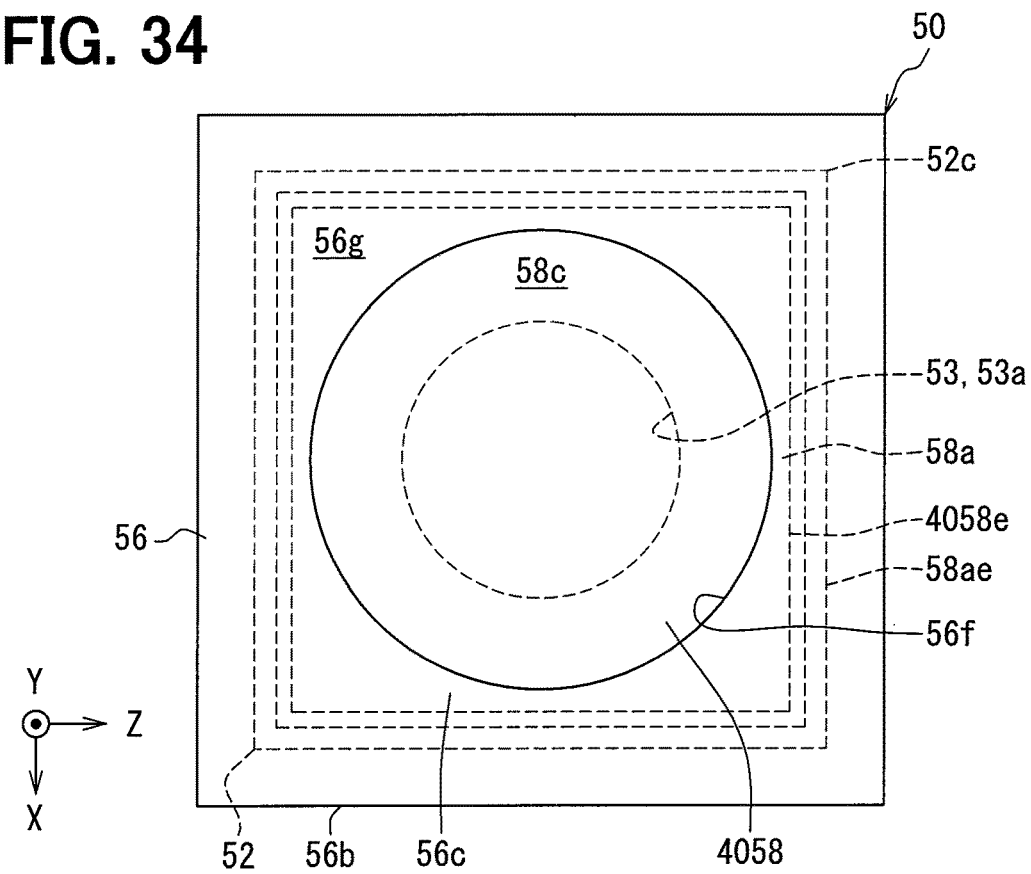
FIG. 34 is a diagram illustrating a plan view showing a modification 6 of the sensor unit relating to FIG. 18.

In a modification 5 relating to the second, the third, and the sixth embodiments, in planar view in Y direction, the body connecting portion 2058*d* may be formed as, for example, a rectangular belt shape instead of a circle belt shape. In a modification 6 relating to the fourth to the sixth embodiments, in planar view in Y direction, the cover connecting portion 5058*e* may be formed as, for example, a rectangular belt shape instead of a circle belt shape. FIG. 33 shows the modification 5 relating to the second embodiment. FIG. 34 shows the modification 6 relating to the fourth embodiment.

Figure 35:
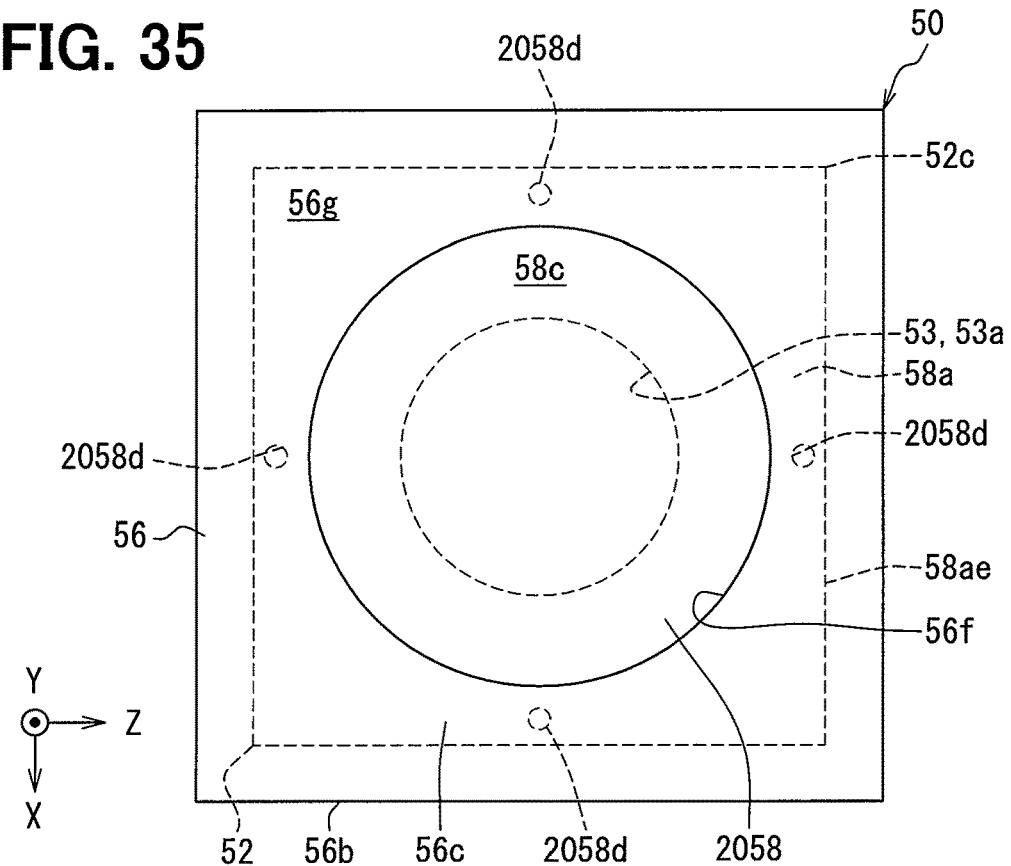
FIG. 35 is a diagram illustrating a plan view showing a modification 7 of the sensor unit relating to FIG. 13.
Figure 36:
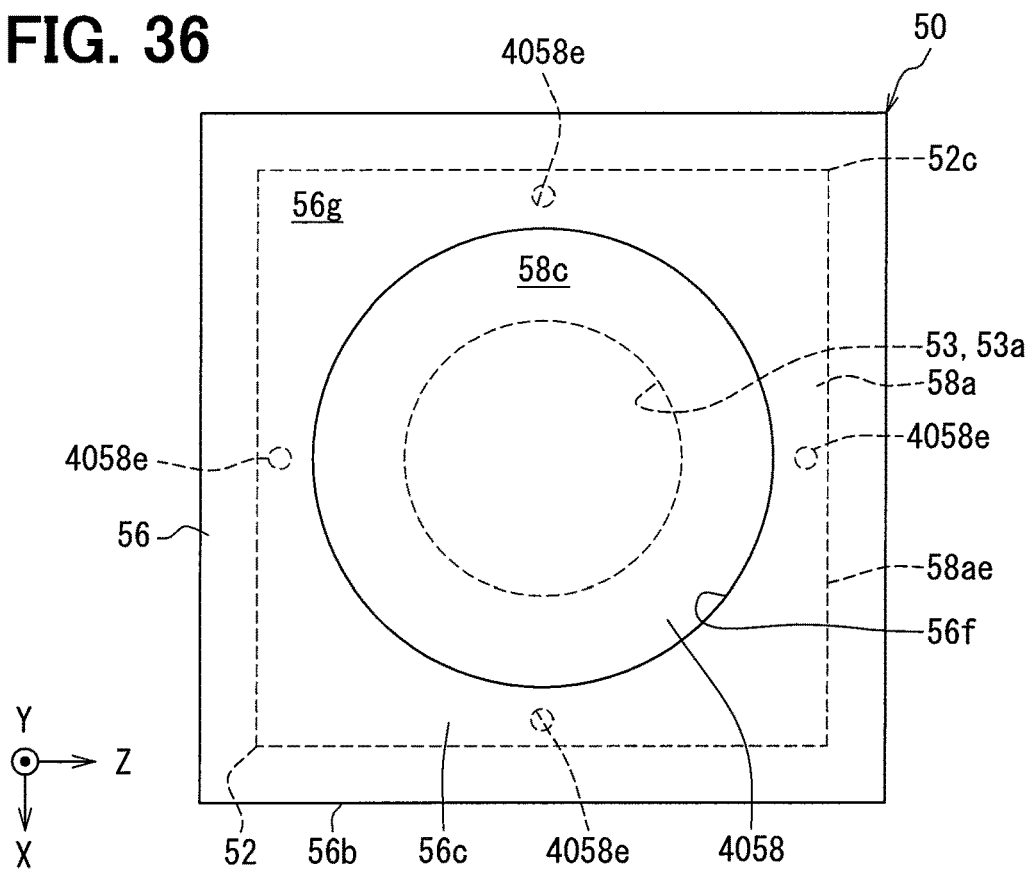
FIG. 36 is a diagram illustrating a plan view showing a modification 8 of the sensor unit relating to FIG. 18.

In a modification 7 relating to the second, the third, and the sixth embodiments, as shown in FIG. 35, a plurality of the body connecting portions 2058*d* may be provided at a predetermined gap in a circumferential direction on the peripheral portion 58*a*. In a modification 8 relating to the fourth to the sixth embodiments, as shown in FIG. 36, a plurality of the cover connecting portions 4058*e* may be provided at a predetermined gap in a circumferential direction on the peripheral portion 58*a*. FIG. 35 shows the modification 7 relating to the second embodiment. FIG. 36 shows the modification 8 relating to the fourth embodiment.

Figure 37:
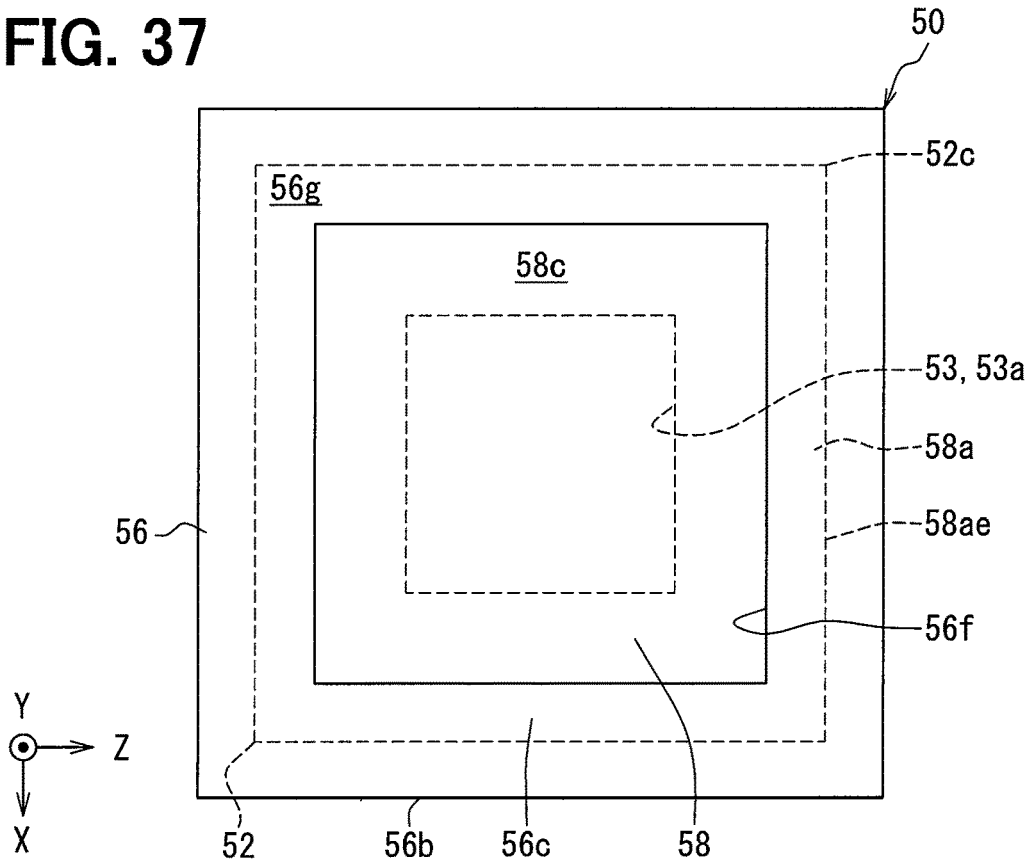
FIG. 37 is a diagram illustrating a plan view showing modifications 9 and 10 of the sensor unit relating to FIG. 7.
Figure 38:
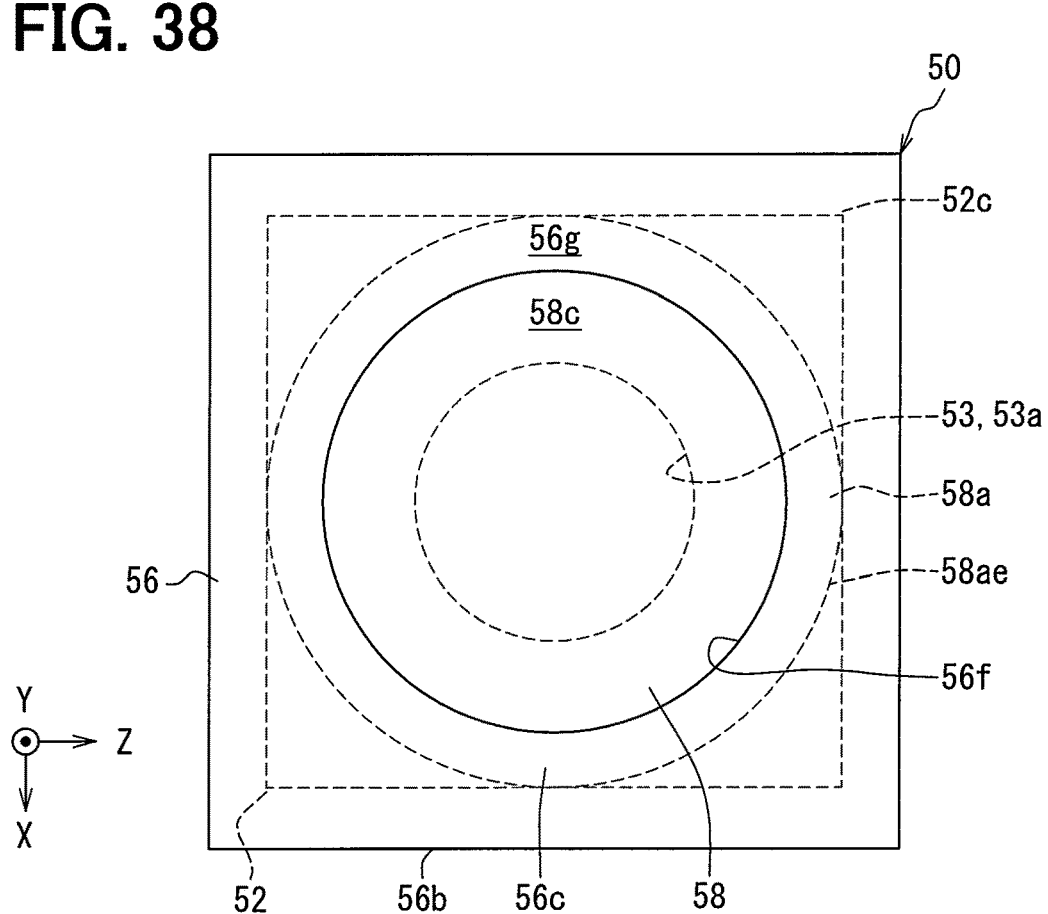
FIG. 38 is a diagram illustrating a plan view showing a modification 11 of the sensor unit relating to FIG. 7.

In a modification 9 relating to the first to the eighth embodiments, in planar view in Y direction, as shown in FIG. 37, the body opening portion 53*a* may be formed as, for example, a rectangular shape instead of a circle shape. In a modification 10 relating to the first to the eighth embodiments, in planar view in Y direction, as shown in FIG. 37, the cover window 56*f* may be formed as, for example, a rectangular shape instead of a circle shape. In a modification 11 relating to the first to the eighth embodiments, in planar view in Y direction, as shown in FIG. 38, the contour of the peripheral portion 53*a* may be formed as, for example, a circle shape instead of a rectangular shape. FIG. 37 shows the modifications 9, 10 relating to the first embodiment, and FIG. 38 shows the modification 11 relating to the first embodiment.

Figure 39:
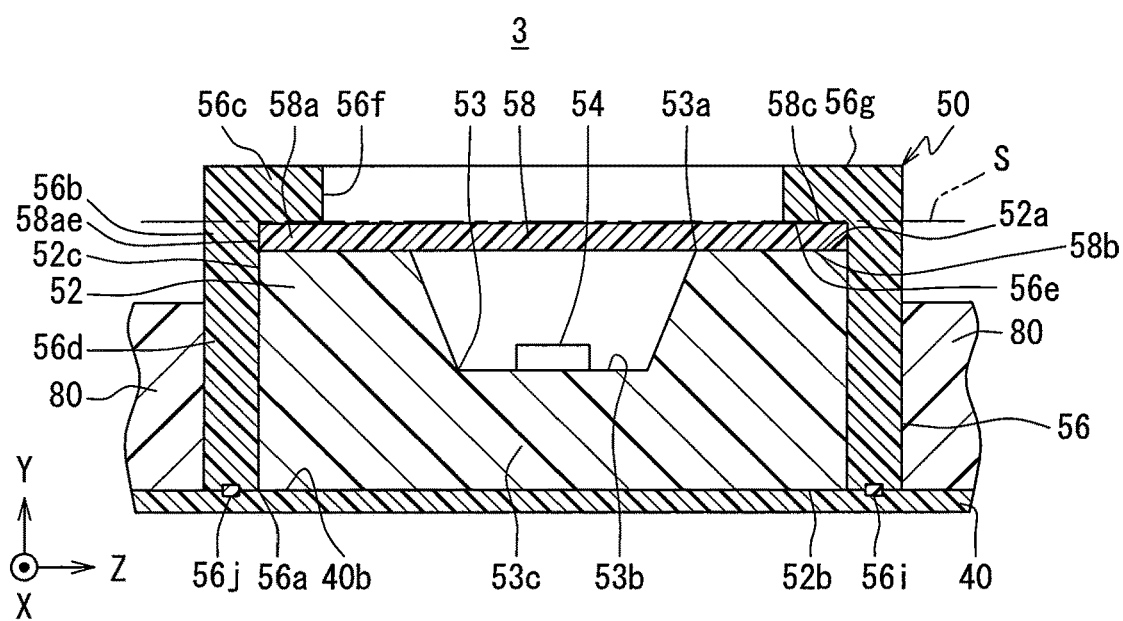
FIG. 39 is a diagram illustrating a cross-sectional view showing a modification 12 of the sensor unit relating to FIG. 6.
Figure 40:
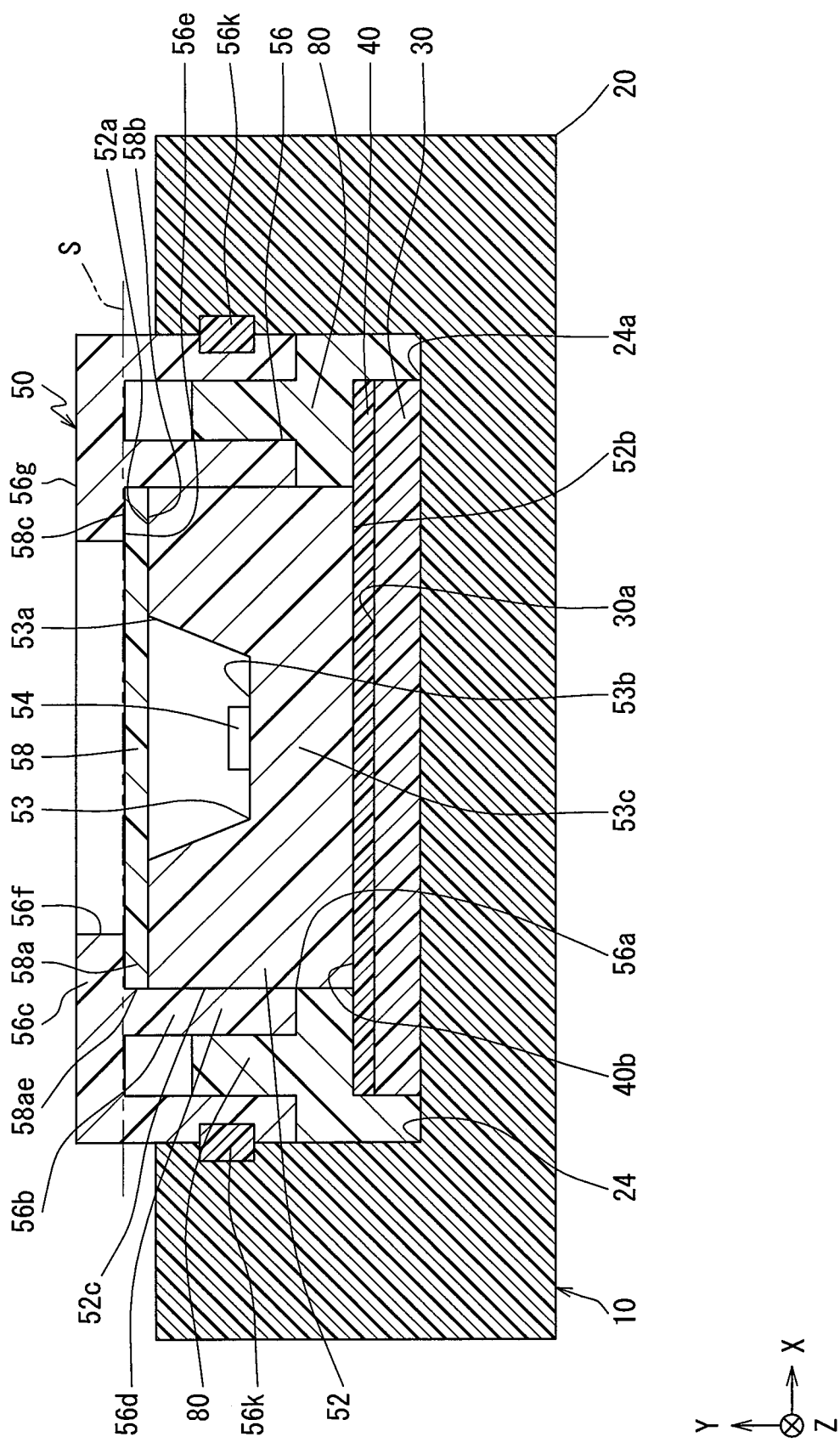
FIG. 40 is a diagram illustrating a cross-sectional view showing a modification 13 of the sensor unit relating to FIG. 6, and corresponding to a cross-sectional view taken along the line XL-XL in FIG. 5.
Figure 41:
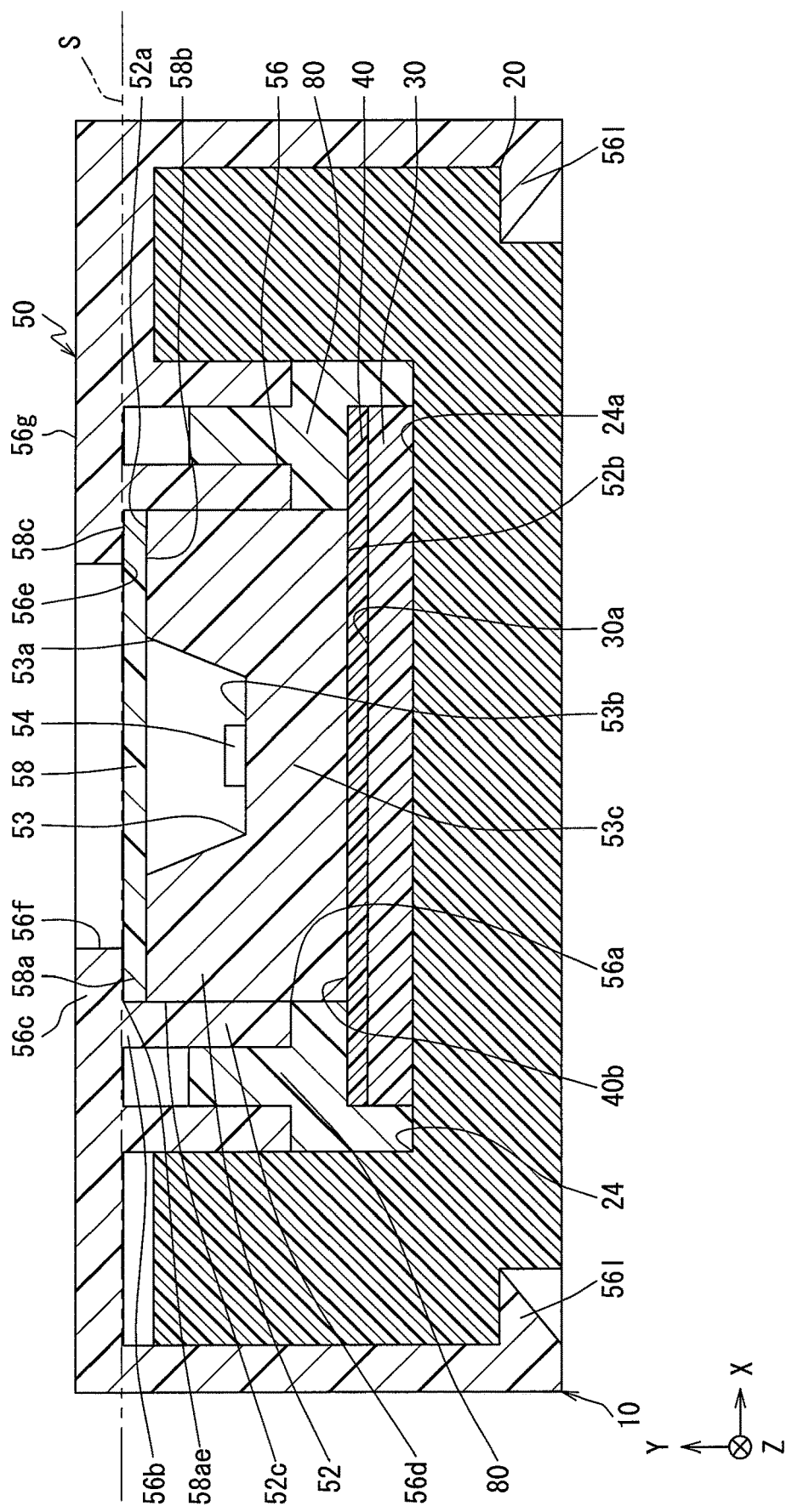
FIG. 41 is a diagram illustrating a cross-sectional view showing a modification 14 of the sensor unit relating to FIG. 6, and corresponding to a cross-sectional view taken along the line XL-XL in FIG. 5.
Figure 42:
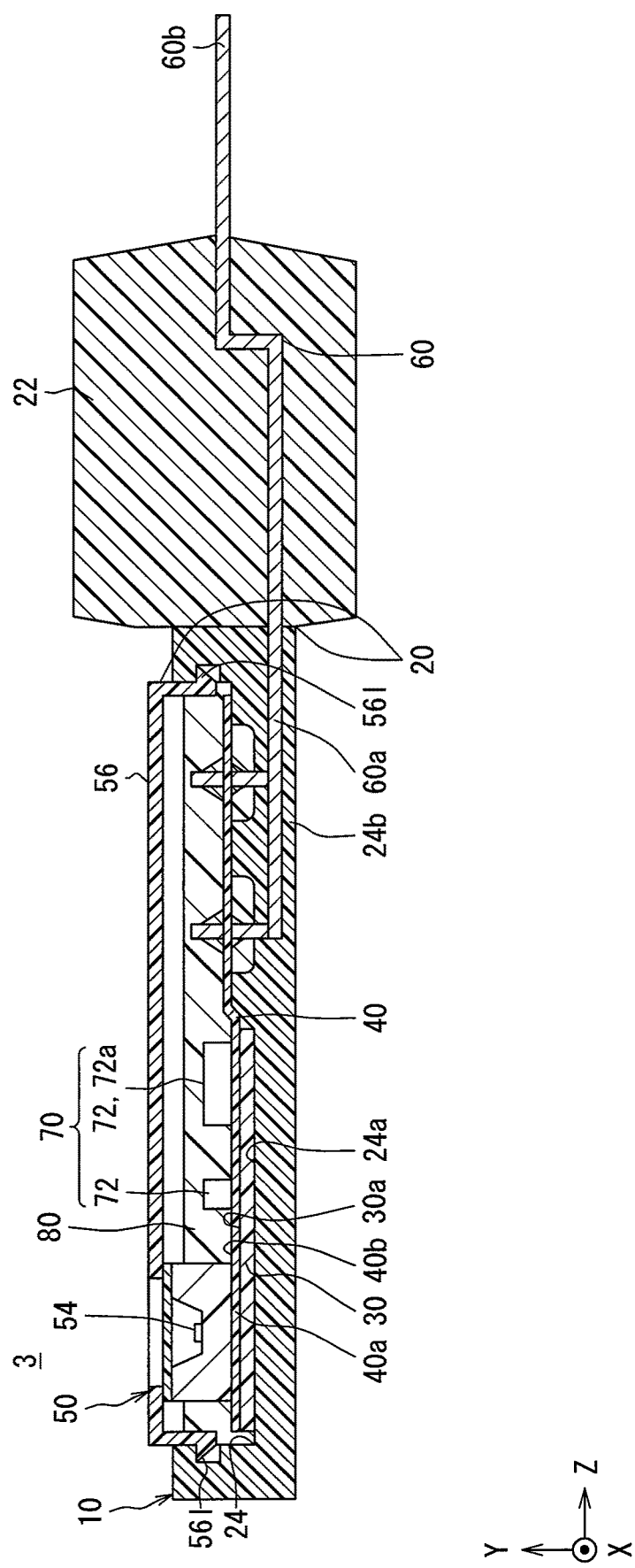
FIG. 42 is a diagram illustrating a cross-sectional view showing a modification 14 of the sensor unit relating to FIG. 5.

In a modification 12 relating to the first to the eighth embodiments, as shown in FIG. 39, the sensor covers 56, 7056 may be connected to the sensor substrates 40, 8040 at the connecting portion 56*j* by, for example, bonded or welded. In a modification 13 relating to the first to the eighth embodiments, as shown in FIG. 40, the sensor covers 56, 7056 may be connected to the sensor cases 20, 8020 at the connecting portion 56*k* by, for example, bonded or welded. In a modification 14 relating to the first to the eighth embodiments, as shown in FIGS. 41 and 42, the sensor covers 56, 7056 may be positioned and fixed to the sensor cases 20, 8020 by means of a projection-recess fitting through a snap fitting of a claw portion 56*l* to the sensor cases 20, 8020. FIGS. 39 and 40 show respectively the modifications 12, 13 relating to the first embodiment, and FIGS. 41 and 42 show the modification 14 relating to the first embodiment.

Figure 43:
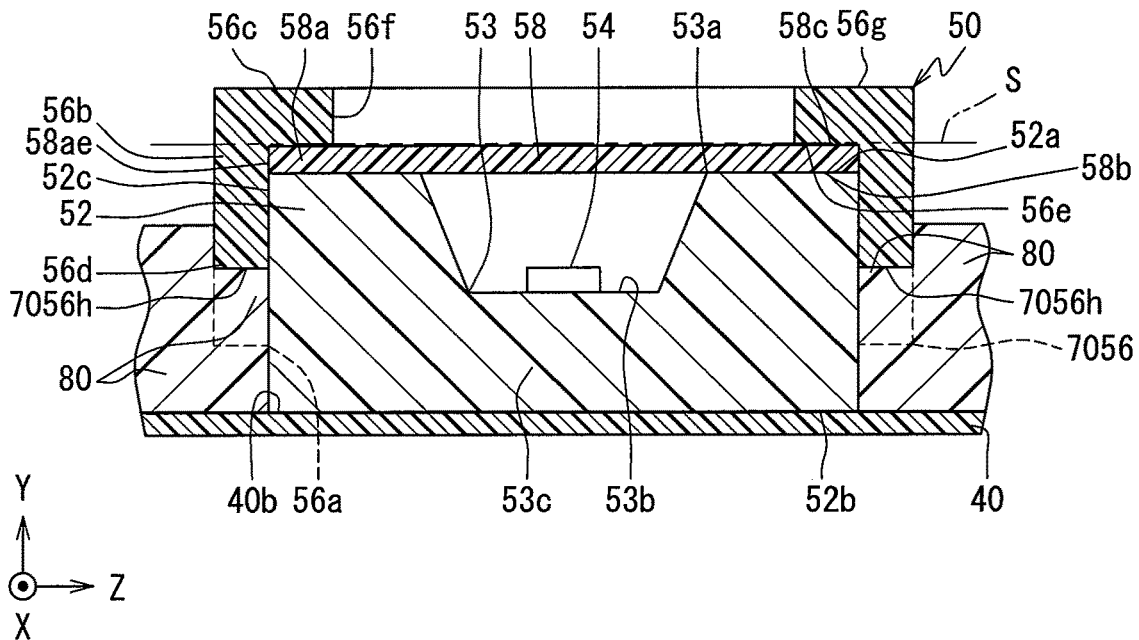
FIG. 43 is a diagram illustrating a cross-sectional view showing a modification 15 of the sensor unit relating to FIG. 6.
Figure 44:
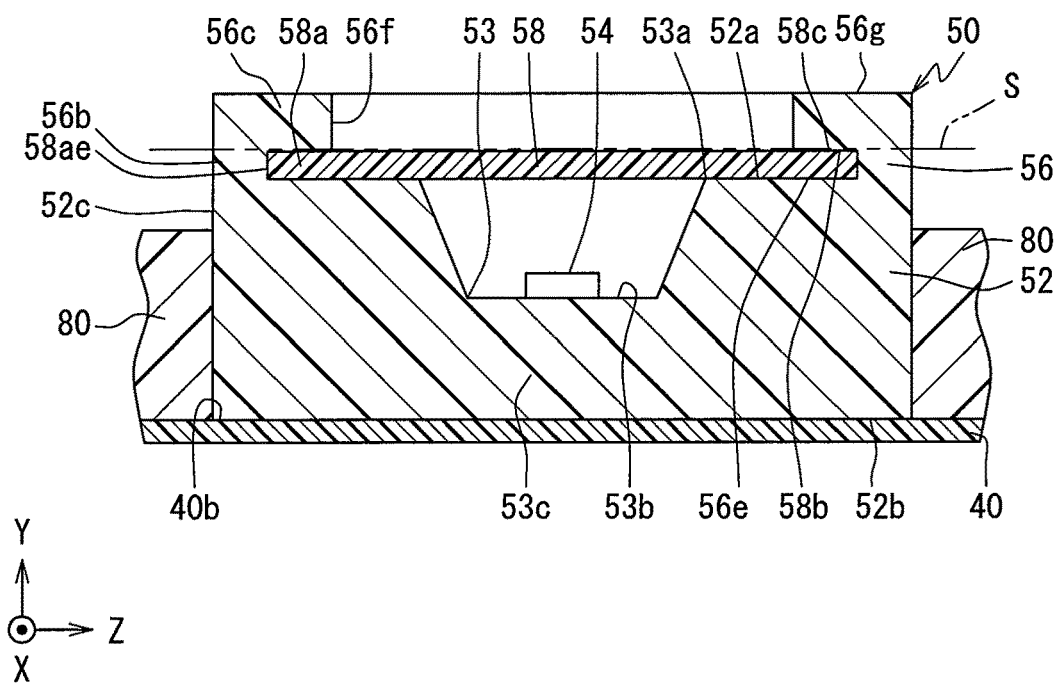
FIG. 44 is a diagram illustrating a cross-sectional view showing a modification 16 of the sensor unit relating to FIG. 6.

In a modification 15 relating to the seventh embodiment, as shown in FIG. 43, a through hole 7056*h* of the sensor cover 7056 may be communicated with the body opening portion 56*a* of the cover peripheral portion 56*b*, since an end portion on the opening side of the body opening portion 56*a* constructed as the embedded portion 56*d* opens. In a modification 16 relating to the first to the eighth embodiments, as shown in FIG. 44, the sensor cover 56, 7056 may be integrally formed with the sensor body 52. In a modification 17 relating to the first to the eighth embodiments, as shown in FIG. 42, the sensor cover 56, 7056 may be constructed as a part of the sensor case 20, 8020. FIGS. 44, 42 show the modifications 16, 17 relating to the first embodiment.

Figure 45:
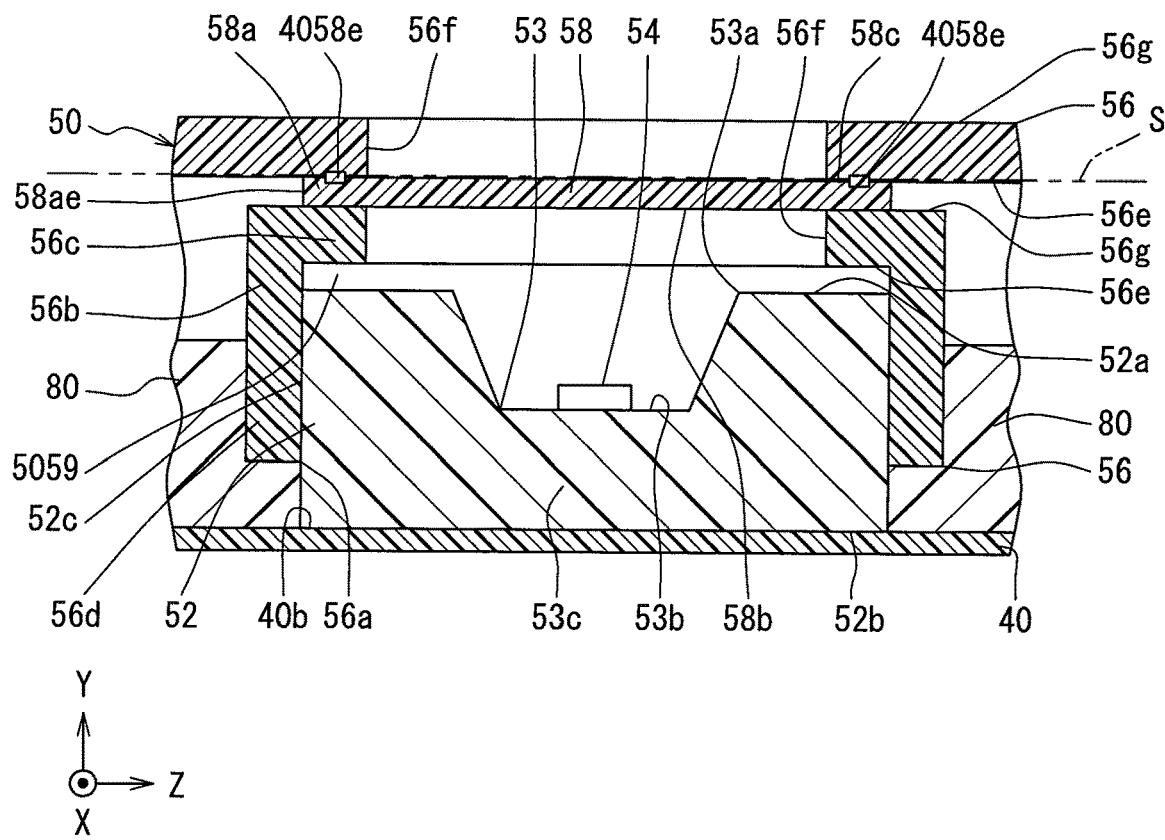
FIG. 45 is a diagram illustrating a cross-sectional view showing a modification 18 of the sensor unit relating to FIG. 6.

In a further modification 18 of the modification 17 relating to the first, the seventh, and the eighth embodiments, as shown in FIG. 45, a first sensor cover 56, 7056 without the cover peripheral portion 56*b* and a second sensor cover 56, 7056 having the cover peripheral portion 56*b* may be provided, and the filter peripheral portion 58*a* may be supported between the first sensor cover 56, 7056 and the second sensor cover 56, 7056. In the modification 18, the filter peripheral portion 58*a* is held between the first sensor cover 56, 7056 and the second sensor cover 56, 7056 in a contacting state. In the modification 18 relating to the fifth embodiment shown in FIG. 45, a bottom wall portion 56*c* of the second sensor cover 56, 7056 is arranged in a body space portion 5059 formed between the filter peripheral portion 58*a* and the sensor body 52. In the modification 18, the filter peripheral portion 58*a* may be connected to at least one of the first sensor cover 56, 7056 and the second sensor cover 56, 7056, or may not be connected to the first sensor cover 56, 7056 and the second sensor cover 56, 7056. In the modification 18 shown in FIG. 45 relating to the fourth embodiment, the filter peripheral portion 58a is connected to the first sensor cover 56, 7056 such that the cover connecting portion 4058e is formed. FIG. 45 shows the modification 18 relating to the first embodiment.

Figure 46:
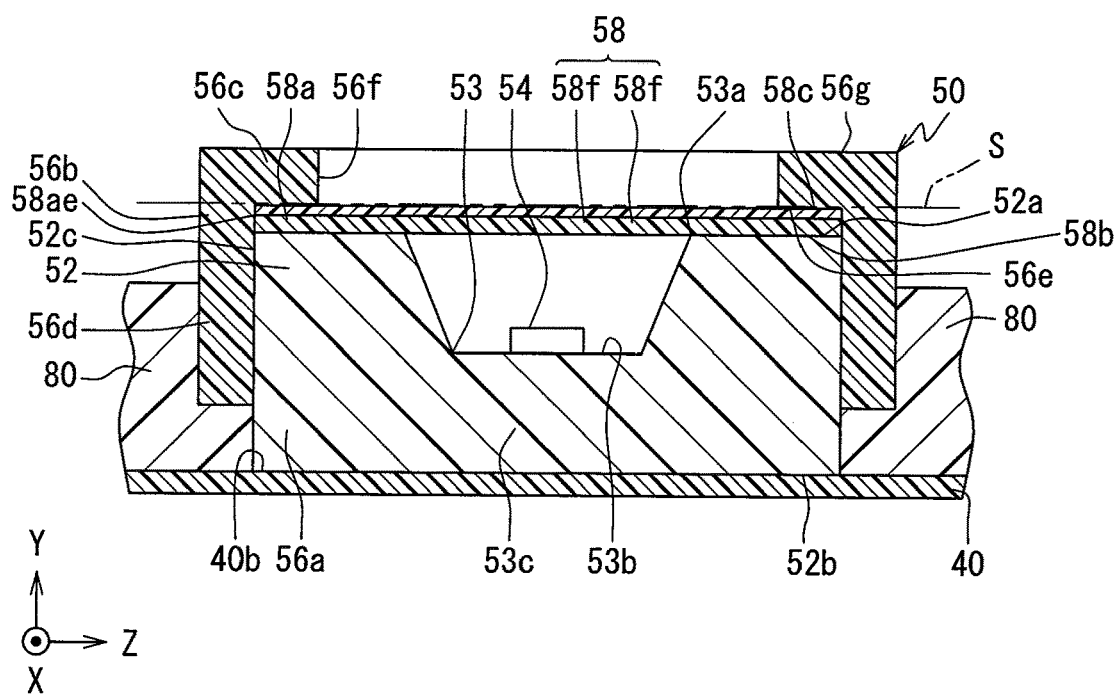
FIG. 46 is a diagram illustrating a cross-sectional view showing a modification 20 of the sensor unit relating to FIG. 6.
Figure 47:
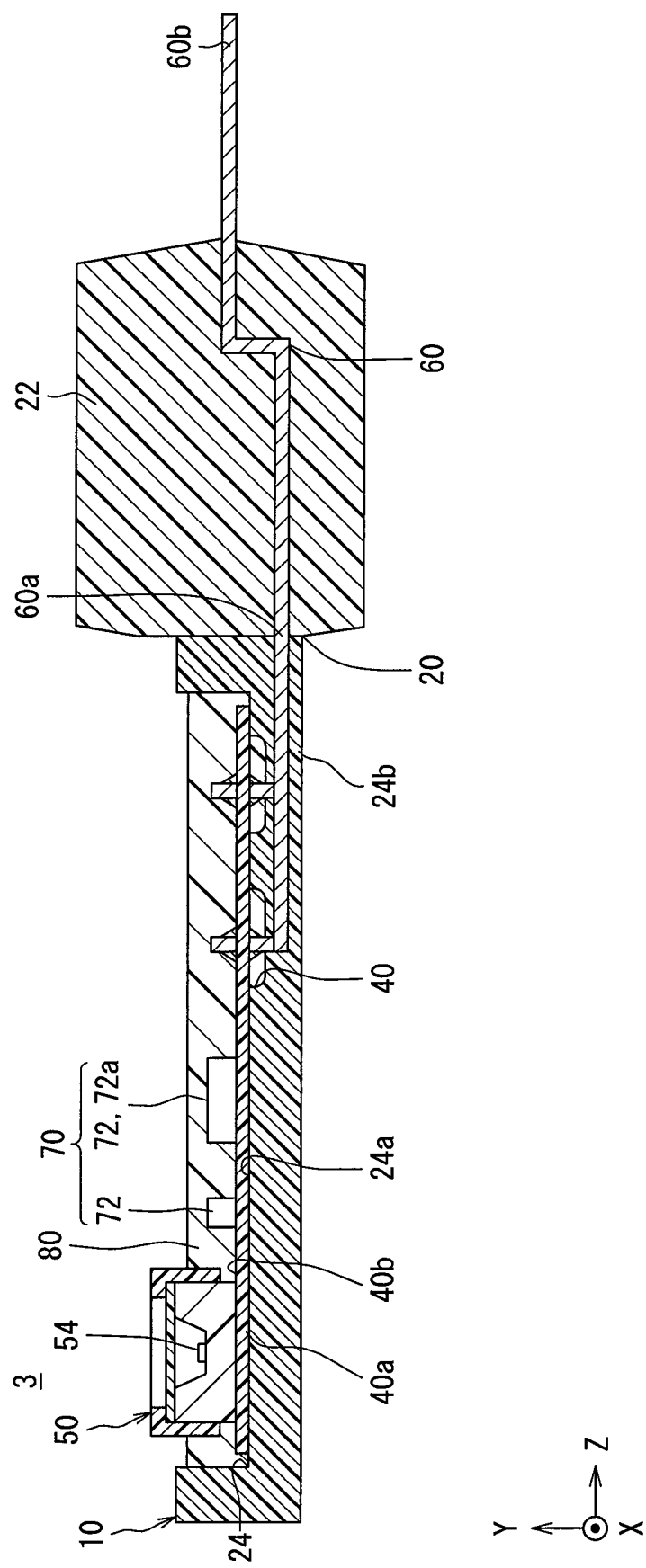
FIG. 47 is a diagram illustrating a cross-sectional view showing a modification 21 of the sensor unit relating to FIG. 5.

In a modification 19 relating to the first to the eight embodiments, the sensor filters 58, 2058, 3058, 4058, 5058, 6058 are not only a porous filter made of PTFE but also, for example, a waterproof filter or a air-permeable filter. The filter used in the second to the sixth embodiments may be a fibrous filter made of other material by considering a bonding property. In a modification 20 relating to the first to the eight embodiments, as shown in FIG. 46, the sensor filters 58, 2058, 3058, 4058, 5058, 6058 are made from a plurality of filter elements 58f, each of which is different from each other as for a material, a roughness, and/or a thickness. In a modification 21 relating to the first to the eight embodiments, as shown in FIG. 47, a reinforcing plate 30 may be omitted, because the sensor substrate 40, 8040 is made from a hard substrate, such as a glass epoxy substrate instead of the soft flexible substrate. FIGS. 46, 47 show respectively the modifications 20, 21 relating to the first embodiment.

Figure 48:
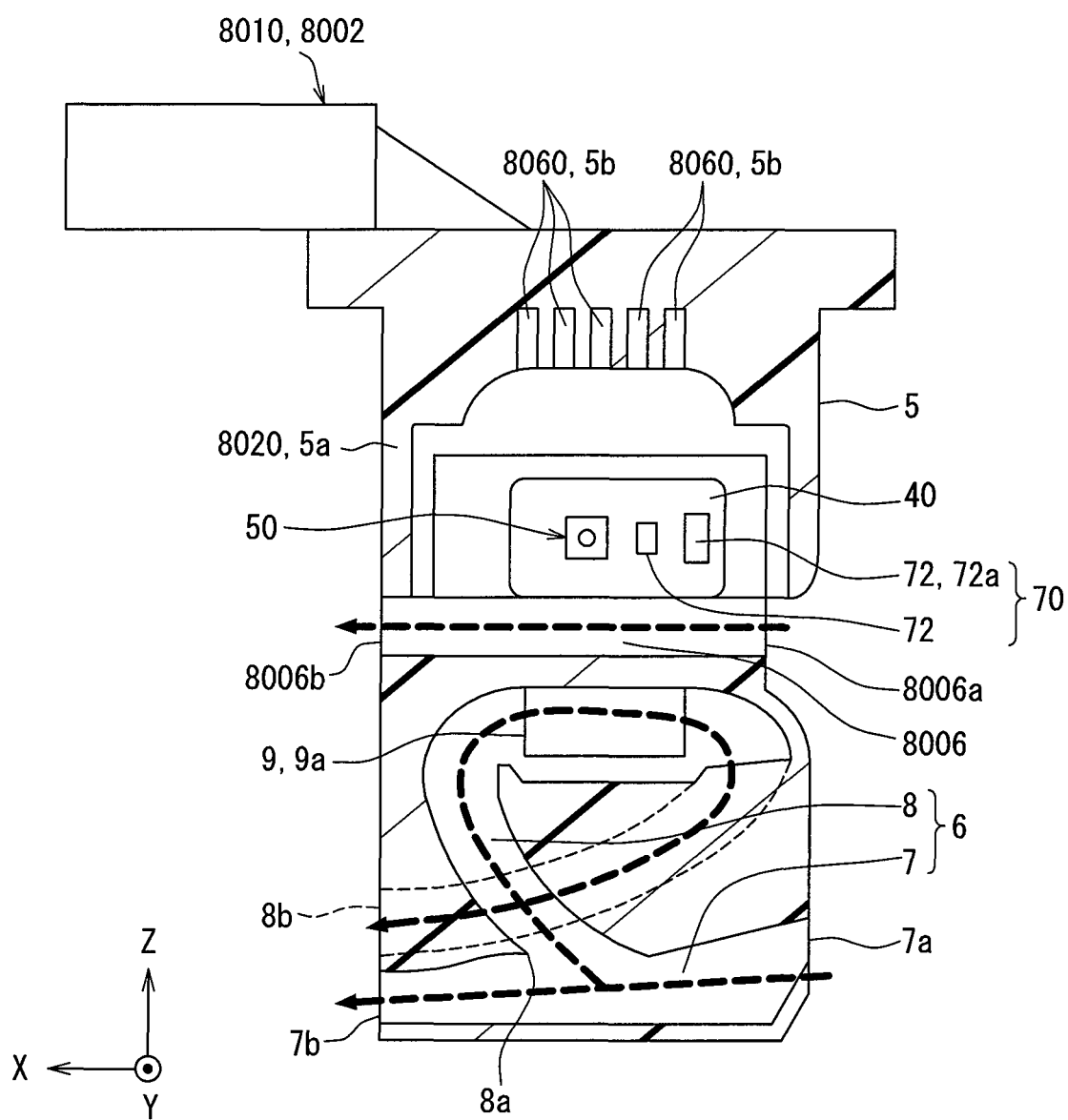
FIG. 48 is a diagram illustrating a partial cross-sectional view showing a modification 22 of the air physical quantity sensor attached to an air flow detection unit relating to FIG. 27.

In a modification 22 relating to the eighth embodiment, as shown in FIG. 48, another bypass passage 8006 is configured to separate from the bypass passage 6, and the bypass passage 8006 has an inlet 8006a and an outlet 8006b, both of which expose the intake passage 3. The bypass passage 8006 is referred to as the flow passage. The sensor unit 50 may be exposed to the bypass passage 8006. In the modification 22, a sensor substrate 40, on which the sensor element 9a and the circuit module 9b are not mounted, is applied as described in the first embodiment.

Figure 49:
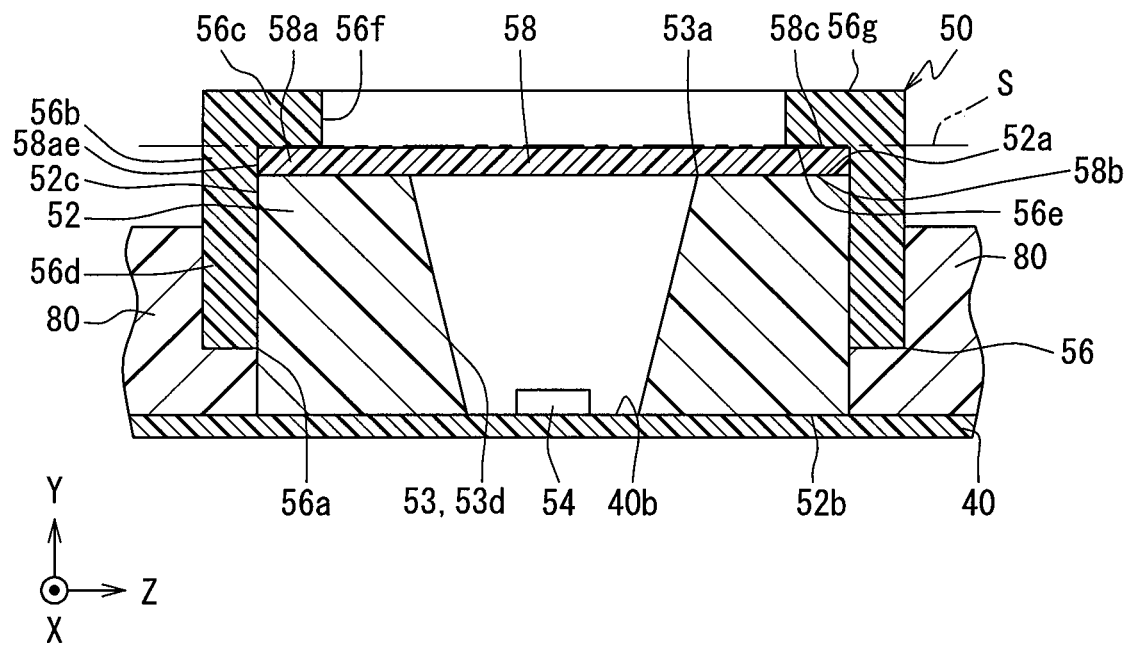
FIG. 49 is a diagram illustrating a cross-sectional view showing a modification 23 of the sensor unit relating to FIG. 6.
Figure 50:
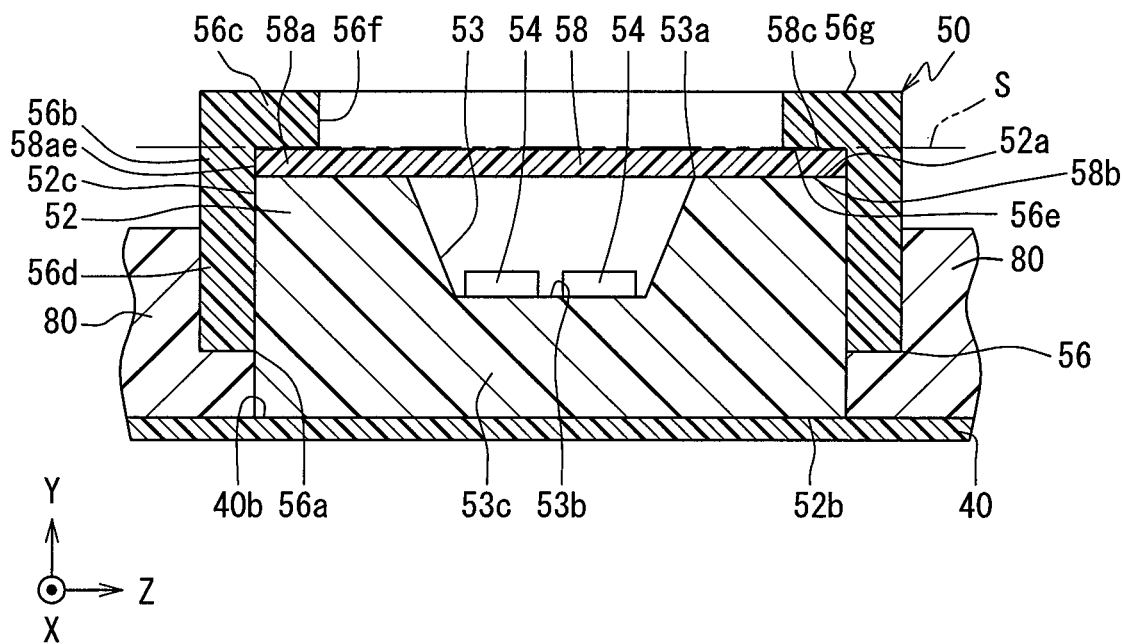
FIG. 50 is a diagram illustrating a cross-sectional view showing a modification 25 of the sensor unit relating to FIG. 6.

In a modification 23 relating to the first to the eighth embodiments, as shown in FIG. 49, a hole portion 53d penetrates in Y direction through the sensor body 52, and the hole portion 53d is covered by the sensor substrate 40, on which the sensor element 54 is mounted. The body recess 53 may be formed as being surrounded by the hole portion 53d and the sensor substrate 40. In a modification 24 relating to the first to the eighth embodiments, the sensor element 54 may detect a specified physical quantity, such as temperature, pressure, thermal conductivity, density, or flow amount for air except for the air humidity. In a modification 25 relating to the first to the eighth embodiments, as shown in FIG. 50, a plurality of the sensor elements 54 which detect the different physical quantity or detect same physical quantity may be housed in the body recess 53. FIGS. 49, 50 show respectively the modification 23, 25 relating to the first embodiment.

What is claimed is:

1. An air physical quantity sensor detecting a specified physical quantity of air flowing in a flow passage, comprising:
   a sensor element configured to output a detection signal in accordance with the specified physical quantity;
   a sensor body having a body recess in which the sensor element is housed, the body recess opening at an body opening portion;
   a sensor cover having a cover window configured to communicate between the flow passage and the body opening portion, the sensor cover covering the sensor body; and
   a sensor filter having a peripheral portion extending along a virtual plane, the sensor filter filtering an air flowing from the flow passage to the body recess through the body opening portion and the cover window, wherein
   in a projection view with respect to the virtual plane, the body opening portion and the cover window are positioned within a filtering area which is defined as an inner side with respect to a contour of the filter peripheral portion, such that the filter peripheral portion is positioned between the sensor body and the sensor cover, and contacts at least one of the sensor body and the sensor cover.

2. The air physical quantity sensor according to claim 1, wherein
   the filter peripheral portion includes a body connecting portion connected to the sensor body, and
   the body connecting portion is positioned within the filtering area in the projection view.

3. The air physical quantity sensor according to claim 2, wherein
   the filter peripheral portion is provided to have a cover space portion between the sensor cover and the filter peripheral portion.

4. The air physical quantity sensor according to claim 1, wherein
   the filter peripheral portion includes a cover connecting portion connected to the sensor cover, and
   the cover connecting portion is positioned within the filtering area in the projection view.

5. The air physical quantity sensor according to claim 4, wherein
   the filter peripheral portion is provided to have a body space portion between the sensor body and the filter peripheral portion.

6. The air physical quantity sensor according to claim 1, wherein
   the filter peripheral portion is interposed between the sensor body and the sensor cover.

7. The air physical quantity sensor according to claim 1, wherein
   the body opening portion is positioned in the cover window in the projection view.

8. The air physical quantity sensor according to claim 1, wherein
   the sensor filter filters the air flowing in the intake passage referred to as the flow passage in a combustion engine.

9. The air physical quantity sensor according to claim 1, wherein
   the sensor filter filters an air in the flow passage, in which a part of the air flowing in the intake passage in a combustion engine flows.

10. The air physical quantity sensor according to claim 1, further comprising,
    an another sensor element configured to detect a specified quantity, which is different from the specified quantity detected by the sensor element; and
    a sensor substrate on which the another sensor element is mounted, wherein
    the sensor substrate supports the sensor body.

* * * * *